United States Patent [19]

Carrozza et al.

[11] Patent Number: 5,463,058
[45] Date of Patent: Oct. 31, 1995

[54] SILOXANE DERIVATIVES OF 2,2,6,6-TETRAMETHYLPIPERIDINE COMPOUNDS AS STABILIZERS

[75] Inventors: Primo Carrozza, Verona; Giovanni Da Roit, Bologna, both of Italy

[73] Assignee: Ciba-Geigy Corporation, Tarrytown, N.Y.

[21] Appl. No.: 391,330

[22] Filed: Feb. 21, 1995

Related U.S. Application Data

[63] Continuation of Ser. No. 207,532, Mar. 7, 1994, abandoned.

[30] Foreign Application Priority Data

Mar. 11, 1993 [IT] Italy ................... MI93A0469

[51] Int. Cl.⁶ .............. C07D 211/18; C07D 211/36; C07D 211/40; C07F 7/02
[52] U.S. Cl. .............. 546/14; 544/110; 546/15; 546/16; 546/188; 546/192; 556/407
[58] Field of Search .............. 546/14, 15, 188, 546/16, 192; 544/110; 556/407

[56] References Cited

U.S. PATENT DOCUMENTS

| | | | |
|---|---|---|---|
| 4,177,186 | 12/1979 | Rody et al. | 546/14 |
| 4,210,578 | 7/1980 | Rody et al. | 528/28 |
| 4,692,486 | 9/1987 | Gugumus | 524/100 |
| 4,859,759 | 8/1989 | Maycock et al. | 546/14 |
| 4,895,885 | 1/1990 | Foster et al. | 524/99 |
| 4,946,880 | 8/1990 | Costanzi et al. | 524/96 |
| 4,948,888 | 8/1990 | Greco et al. | 544/69 |

FOREIGN PATENT DOCUMENTS

| | | |
|---|---|---|
| 2118666 | 9/1994 | Canada . |
| 0080431 | 6/1983 | European Pat. Off. . |
| 0162524 | 11/1985 | European Pat. Off. . |
| 0244026 | 11/1987 | European Pat. Off. . |
| 0343717 | 11/1989 | European Pat. Off. . |
| 0388321 | 9/1990 | European Pat. Off. . |
| 0461071 | 12/1991 | European Pat. Off. . |
| 0491659 | 6/1992 | European Pat. Off. . |
| 0234682 | 4/1986 | Germany . |
| 0234683 | 4/1986 | Germany . |
| 101368 | 7/1988 | Taiwan . |
| 1326889 | 8/1973 | United Kingdom . |
| 1502557 | 3/1978 | United Kingdom . |

OTHER PUBLICATIONS

Chemical Abstract, vol. 80, #121668, 1973.
Rody et al., Chemical Abstract, vol. 86, #73762, 1976.
Chem. Abst., 115:160562 (1991).
Derwent 90–284499/38, 1990.
Chem. Abst., 106:5979t (1987).
Derwent 86–205176/32, 1986.
Derwent 86–205177/32, 1986.
Chem. Abst., 106:19478r (1987).
C.A. 78(10) 58824y, 1972.
I. Jansen, et al., Acta Polym., 40(2), 121–6 (1989).
C.A. 80(21):119866d, 1974.
C.A. 89(14):111932n, 1978.

*Primary Examiner*—Yogendra N. Gupta
*Attorney, Agent, or Firm*—Michele A. Kovaleski

[57] ABSTRACT

Novel polymethylpiperidine compounds of general formula (I) containing silane groups and effective as light stabilizers, heat stabilizers and oxidation stabilizers for organic materials.

The meanings of $R_1$, $R_2$, $R_3$, $R_4$ and n are defined in the text.

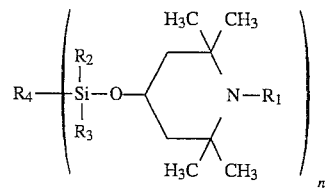

(I)

6 Claims, No Drawings

SILOXANE DERIVATIVES OF 2,2,6,6-TETRAMETHYLPIPERIDINE COMPOUNDS AS STABILIZERS

This application is a continuation of Ser. No. 08/207,532, filed on Mar. 7, 1994 now abandoned.

The present invention relates to novel polymethylpiperidine compounds containing silane groups, their use as light stabilisers, heat stabilisers and oxidation stabilisers for organic materials, particularly synthetic polymers, and organic materials thus stabilised.

The stabilisation of synthetic polymers with derivatives of 2,2,6,6-tetramethylpiperidine containing silane groups has been described in various patents, in particular in U.S. Pat. Nos. 4,177,186, 4,859,759, 4,895,885, 4,946,880 and 4,948,888, in European Patents 162 524, 244 026, 343 717, 388 321, 461 071 and 491 659 and in DD Patents 234 682 and 234,683.

The present invention relates to novel compounds of general formula (I)

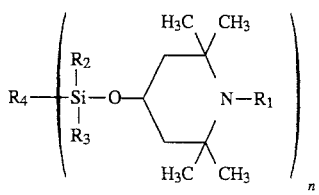

in which $R_1$ is hydrogen, $C_1$–$C_8$alkyl, O·, OH, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or substituted on the phenyl with 1,2 or 3 $C_1$–$C_4$alkyl, or aliphatic $C_1$–$C_8$acyl;

$R_2$ and $R_3$, which may be identical or different, are $C_1$–$C_8$alkyl, phenyl, $C_1$–$C_8$alkoxy or a group of formula (II)

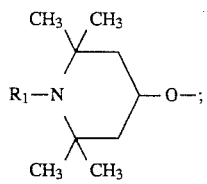

n is 1,2,3 or 4;

if n is 1, $R_4$ is $C_2$–$C_{30}$alkyl, $C_5$–$C_{12}$cycloalkyl which is unsubstituted or substituted with 1, 2 or 3 $C_1$–$C_4$alkyl or one of the groups of formulae (IIIa)–(IIId)

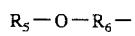

$R_5$—O—$R_6$—   (IIIa)

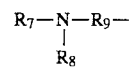

$R_7$—N—$R_9$—
      |
      $R_8$   (IIIb)

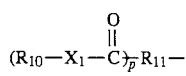

$$(R_{10}—X_1—\overset{O}{\overset{\|}{C}})_p\,R_{11}—$$   (IIIc)

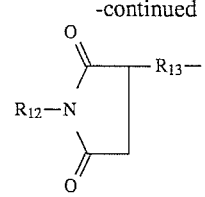

in which $R_5$ is $C_1$–$C_{18}$alkyl, $C_3$–$C_{30}$alkyl interrupted by one or more oxygen atoms, $C_5$–$C_{12}$cycloalkyl which is unsubstituted or substituted with 1,2 or 3 $C_1$–$C_4$alkyl, phenyl which is unsubstituted or substituted with 1,2 or 3 $C_1$–$C_4$alkyl or with $C_1$–$C_4$alkoxy, $C_7$–$C_9$phenylalkyl which is unsubstituted or substituted on the phenyl with 1,2 or 3 $C_1$–$C_4$alkyl, a group of formula (IV)

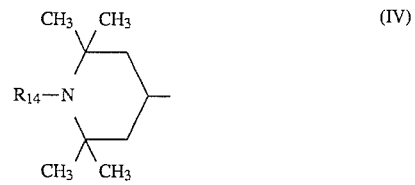

where $R_{14}$ has any one of the meanings given for $R_1$, or $R_5$ is aliphatic, cycloaliphatic or aromatic acyl containing not more than 22 carbon atoms or a group

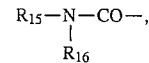

$R_{15}$—N—CO—,
      |
      $R_{16}$ where $R_{15}$ and $R_{16}$, which may be identical or different, are hydrogen, $C_1$–$C_{18}$alkyl, $C_5$–$C_{12}$cycloalkyl which is unsubstituted or substituted with 1,2 or 3 $C_1$–$C_4$alkyl, $C_7$–$C_9$phenylalkyl which is unsubstituted or substituted on the phenyl with 1,2 or 3 $C_1$–$C_4$alkyl or a group of formula (IV), or

$R_{15}$—N—
      |
      $R_{16}$ is a heterocyclic group with 5–7 members, or one of the groups of formulae (Va)–(Vc)

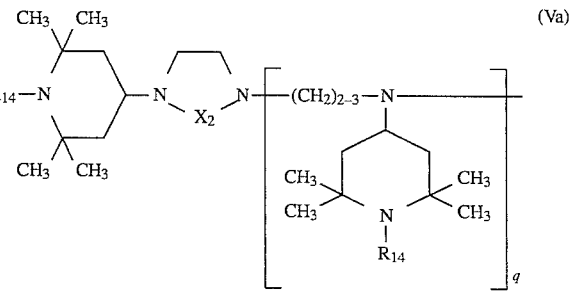

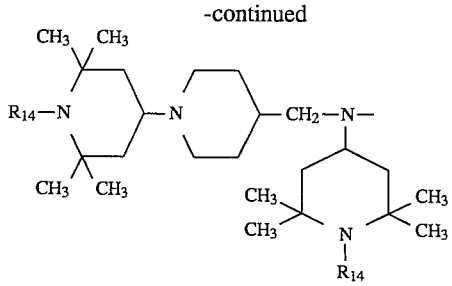
(Vb)

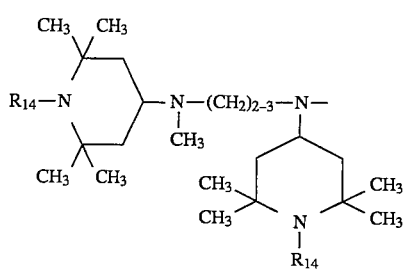
(Vc)

in which $R_{14}$ is as defined above, $X_2$ is —CH$_2$CH$_2$—, —CO—, —COCO— or —COCH$_2$CO— and q is zero or 1; $R_6$ is $C_2$–$C_{18}$alkylene; $R_7$ and $R_8$, which may be identical or different, are as defined above for $R_{15}$ and $R_{16}$, or $R_7$ is also ($C_1$–$C_{18}$alkoxy)carbonyl or aliphatic, cycloaliphatic or aromatic acyl containing not more than 22 carbon atoms, or

is a heterocyclic group having 5–7 members or one of the groups of formulae (Va)–(Vc) or one of the groups of formulae (VIa)–(VIc)

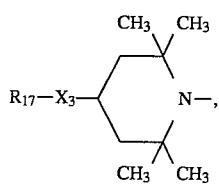
(VIa)

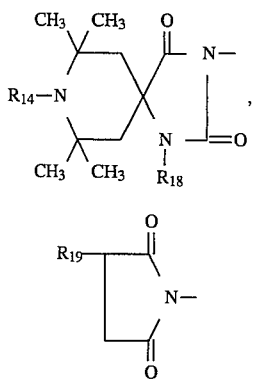
(VIb)

(VIc)

in which $X_3$ is —O— or

where $R_{20}$ is as defined above for $R_{15}$ and $R_{16}$; $R_{17}$ is as defined above for $R_7$ or $R_{17}$—$X_3$— is hydrogen or a nitrogen-containing heterocyclic group having 5–7 members, with the free valency on the nitrogen atom, or the group

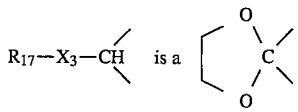

group, $R_{14}$ is as defined above, $R_{18}$ is hydrogen, methyl, acetyl or benzyl and $R_{19}$ is hydrogen or $C_1$–$C_{30}$alkyl; $R_9$ is $C_3$–$C_{18}$alkylene; $R_{10}$ is $C_1$–$C_{18}$alkyl, $C_5$–$C_{12}$cycloalkyl which is unsubstituted or substituted with 1,2 or 3 $C_1$–$C_4$alkyl, $C_7$–$C_9$phenylalkyl which is unsubstituted or substituted on the phenyl with 1,2 or 3 $C_1$–$C_4$alkyl or a group of formula (IV), or $R_{10}$ is a group of formula (VII)

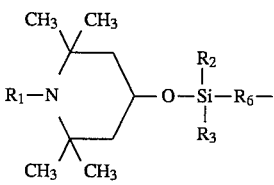
(VII)

with $R_1$, $R_2$, $R_3$ and $R_6$ as defined above; $X_1$ is as defined above for $X_3$ or $R_{10}X_1$— is a nitrogen-containing heterocyclic group having 5–7 members, with the free valency on the nitrogen atom, or one of the groups of formulae (Va)–(Vc) or (VIa)–(VIc); p is 1,2 or 3 and, if p is 1, $R_{11}$ is $C_2$–$C_{18}$alkylene, if p is 2, $R_{11}$ is $C_2$–$C_{20}$alkanetriyl, $C_5$–$C_7$cycloalkanetriyl or $C_7$–$C_9$bicycloalkanetriyl and, if p is 3, $R_{11}$ is $C_3$–$C_6$alkanetetrayl; $R_{12}$ is as defined above for $R_{15}$ and $R_{16}$ and $R_{13}$ is a direct bond or $C_1$–$C_{30}$alkylene; if n is 2, $R_4$ is $C_2$–$C_{12}$alkylene, $C_4$–$C_{22}$alkylene interrupted by an oxygen atom or by an

group, where $R_{21}$ is as defined above for $R_7$, or $R_4$ is one of the groups of formulae (VIIIa)–(VIIIc)

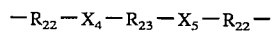
(VIIIa)

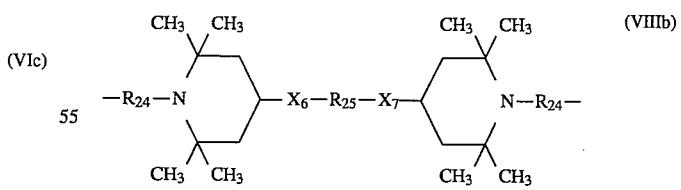
(VIIIb)

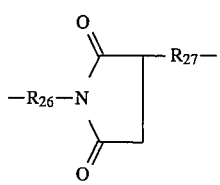
(VIIIc)

in which $X_4$ and $X_5$, which may be identical or different, are —O— or $$R_{28}-N-,$$

where $R_{28}$ is as defined above for $R_7$; $R_{22}$ is $C_2$–$C_{18}$alkylene or a —$C_rH_{2r}CO$— group, where r is an integer from 2 to 18 and the carbonyl group is bonded to $X_4$ or $X_5$; $R_{23}$ is $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$ alkylene), $C_1$–$C_4$alkylenedi($C_5$-$C_7$cycloalkylene), isopropylidene-dicyclohexylene, phenylene which is unsubstituted or substituted by 1 or 2 $C_1$–$C_4$alkyl, phenylenedi($C_1$–$C_4$alkylene), $C_2$–$C_4$alkylidenediphenylene or a group of formula (IXa) or (IXb)

$$\text{(IXa)}$$

in which $R_{29}$ is hydrogen or $C_1$–$C_4$alkyl and $R_{30}$ is $C_2$–$C_{12}$alkylene, $C_4$–$C_{12}$alkylene interrupted by one or more oxygen atoms or phenylenedi($C_1$–$C_4$alkylene) or, if $R_{22}$ is $C_2$–$C_{18}$alkylene, $R_{23}$ is also carbonyl, a $$-\overset{O}{\underset{\|}{C}}-R_{31}-\overset{O}{\underset{\|}{C}}- \quad \text{or} \quad -\overset{O}{\underset{\|}{C}}-O-R_{32}-O-\overset{O}{\underset{\|}{C}}- \quad \text{or}$$

$$-\overset{O}{\underset{\|}{C}}-\underset{R_{33}}{N}-R_{34}-\underset{R_{35}}{N}-\overset{O}{\underset{\|}{C}}-$$

group, where $R_{31}$ is a direct bond, $C_1$–$C_{12}$alkylene, $C_2$–$C_{20}$alkylidene, $C_5$–$C_7$cycloalkylene or phenylene which is unsubstituted or substituted with 1 or 2 $C_1$–$C_4$alkyl, $R_{32}$ and $R_{34}$ are $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_5$–$C_4$alkylene), $C_1$–$C_4$alkylenedi($C_5$–$C_7$cycloalkylene), $C_2$–$C_4$alkylenedi($C_5$–$C_7$cycloalkylene) or a group of formula (IXa) or (IXb), and $R_{33}$ and $R_{35}$, which may be identical or different, are as defined above for $R_{15}$ and $R_{16}$, or the —$R_{23}$—$X_5$— group is a group or the —$X_4$—$R_{23}$—$X_5$— group is a group with $X_2$ as defined above or a group; $R_{24}$ is $C_3$–$C_{18}$alkylene; $X_6$ and $X_7$, which may be identical or different, are as defined above for $X_4$ and $X_5$; $R_{25}$ is $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), carbonyl, or $$-\overset{O}{\underset{\|}{C}}.R_{31}.\overset{O}{\underset{\|}{C}}- \quad \text{or} \quad -\overset{O}{\underset{\|}{C}}-O-R_{32}-O-\overset{O}{\underset{\|}{C}}-$$

group, with $R_{31}$ and $R_{32}$ as defined above, or the —$X_6$—$R_{25}$—$X_7$— group is an group, where $R_{36}$ is as defined above for $R_7$ and $X_2$ is as defined above, or the $$\text{CH}-X_6-R_{25}-X_7-\text{CH}$$

group is a group; $R_{26}$ is $C_3$–$C_{18}$alkylene or a group of formula (X)

$$\text{(X)}$$

where $R_{37}$ is $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$alkylene) or $C_1$–$C_4$alkylenedi($C_5$–$C_7$cycloalkylene) and $R_{27}$ is a direct bond or $C_1$–$C_{30}$alkylene; if n is 3, $R_4$ is one of the groups of formulae (XIa)–(XIe)

$$R_{38}\!\!-\!\!(\!O\!-\!R_{39}\!)_{\overline{3}} \quad \text{(XIa)}$$

$$\begin{array}{c}-R_{40}-N-R_{42}-\\ |\\ R_{41}\end{array} \quad \text{(XIb)}$$

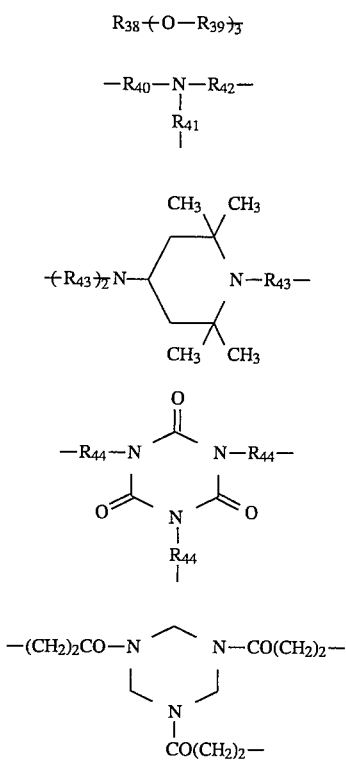

(XIc)

(XId)

(XIe)

in which $R_{38}$ is $C_3$–$C_{12}$alkanetriyl or aliphatic or aromatic triacyl containing not more than 12 carbon atoms; $R_{39}$ is $C_2$–$C_{18}$alkylene or, if $R_{38}$ is $C_3$–$C_{12}$alkanetriyl, $R_{39}$ is also a —$C_sH_{2s}CO$— group where s is an integer from 2 to 18 and the carbonyl group is bonded to the oxygen atom; $R_{40}$, $R_{41}$ and $R_{42}$, which may be identical or different, are $C_3$–$C_{18}$alkylene or $R_{40}$ is also a

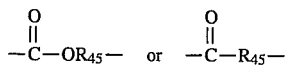

group, where the carbonyl group is bonded to the nitrogen atom and $R_{45}$ is $C_2$–$C_{18}$alkylene; $R_{43}$ is $C_3$–$C_{18}$alkylene and $R_{44}$ is $C_2$–$C_6$alkylene; if n is 4, $R_4$ is one of the groups of formulae (XIIa)–(XIIc)

$$R_{46}\!\!-\!\!(\!O R_{47}\!)_{\overline{4}} \quad \text{(XIIa)}$$

$$\!\!-\!\!(R_{48}\!)_2\!-\!N\!-\!R_{49}\!-\!N\!-\!(R_{48}\!)_{\overline{2}} \quad \text{(XIIb)}$$

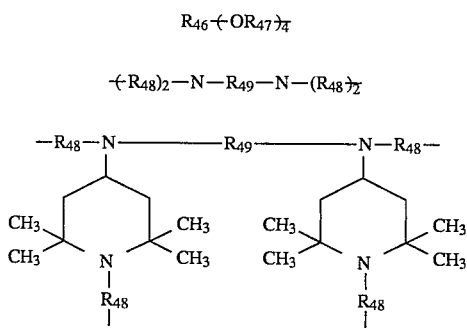

in which $R_{46}$ is $C_4$–$C_6$alkanetetrayl or aliphatic or aromatic tetraacyl containing not more than 12 carbon atoms; $R_{47}$ is $C_2$–$C_{18}$alkylene or, if $R_{46}$ is $C_4$–$C_{12}$alkanetetrayl, $R_{47}$ is also a —$C_sH_{2s}CO$— group as defined above; $R_{48}$ is $C_3$–$C_{18}$alkylene and $R_{49}$ is as defined above for $R_{25}$.

Examples of alkyl containing not more than 30 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl, octadecyl, eicosyl, docosyl, tetracosyl, hexacosyl, octacosyl and triacontyl.

$R_4$ is preferably $C_4$–$C_{28}$, in particular $C_{12}$–$C_{18}$alkyl. Preferred examples of $C_3$–$C_{30}$alkyl interrupted by one or more oxygen atoms are the groups $R_a$—$(OCH_2CH_2)_x$—, in which $R_a$ is $C_1$–$C_{18}$alkyl and x is an integer from 1 to 6.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. For $R_1$ and $R_{14}$, $C_6$–$C_{12}$alkoxy, in particular heptoxy or octoxy, is preferred.

Examples of $C_5$–$C_{12}$cycloalkyl which is unsubstituted or substituted with 1,2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

For $R_1$ and $R_{14}$, examples of $C_5$–$C_{12}$cycloalkoxy are cyclopentoxy, cyclohexoxy, cycloheptoxy, cyclooctoxy, cyclodecyloxy and cyclododecyloxy. Cyclopentoxy and cyclohexoxy are preferred.

For $R_1$ and $R_{14}$, examples of $C_3$–$C_6$alkenyl are allyl, 2-methylallyl, butenyl and hexenyl. Allyl is particularly preferred.

Representative examples of phenyl which is substituted with 1,2 or 3 $C_1$–$C_4$alkyl or with $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl with 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Representative examples of aliphatic, cycloaliphatic or aromatic acyl, containing not more than 22 carbon atoms, are acetyl, propionyl, butyryl, isobutyryl, pentanoyl, hexanoyl, heptanoyl, octanoyl, 2-ethylhexanoyl, decanoyl, undecanoyl, dodecanoyl, tetradecanoyl, hexadecanoyl, octadecanoyl, eicosanoyl, docosanoyl, acryloyl, crotonyl, cyclohexanecarbonyl, benzoyl, t-butylbenzoyl, 3,5-di-t-butyl-4-hydroxybenzoyl and 3-(3,5-di-t-butyl-4-hydroxyphenyl)propionyl.

Preferred examples of the nitrogen-containing heterocyclic groups with 5–7 members and with the free valency on the nitrogen atom are 1-pyrrolidyl, 1-piperidyl, 4-morpholinyl, 4-methyl-1-piperazinyl and 1-hexahydroazepinyl. 4-Morpholinyl is particularly preferred.

Examples of alkylene containing not more than 30 carbon atoms are methylene, ethylene, propylene, trimethylene, 2-methyltrimethylene, tetramethylene, pentylene, hexylene, heptylene, octylene, decylene, undecylene, dodecylene, tetradecylene, hexadecylene, heptadecylene, octadecylene, eicosylene, docosylene, tetracosylene, hexacosylene, octacosylene and triacontylene.

Representative examples of $C_4$–$C_{12}$alkylene interrupted by one or more oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Where $R_4$ is $C_4$–$C_{22}$alkylene interrupted by an oxygen atom, representative examples are 3-oxapentane-1,5-diyl, 3-oxahexane-1,6-diyl, 4-oxaheptane-1,7-diyl, 2,6-dimethyl- 4-oxaheptane-1,7-diyl, 4-oxapentadecane-1,15-diyl or a —(CH$_2$)$_3$—O—R$_b$— group, where R$_b$ is octadecylene.

Where R$_4$ is C$_4$–C$_{22}$alkylene interrupted by an $$R_{21}-N-$$

group, preferred examples are the groups:

$$-(CH_2)_3-N-(CH_2)_3-, \quad -CH_2CHCH_2-N-CH_2CHCH_2- \\ \phantom{-(CH_2)_3-N}|\phantom{-(CH_2)_3-,\quad -CH_2CHCH_2-N-}\phantom{|}\phantom{CH_2CHCH_2-} \\ \phantom{-(CH_2)_3-}R_{21}\phantom{(CH_2)_3-,\quad -CH_2CHCH_2-}CH_3\phantom{-N-}CH_3 \\ \phantom{-(CH_2)_3-N-(CH_2)_3-,\quad -CH_2CHCH_2-}R_{21}$$

and $$-(CH_2)_3-N-R_b \\ \phantom{-(CH_2)_3-}|\phantom{-R_b} \\ \phantom{-(CH_2)_3-}R_{21}$$

where R$_{21}$ and R$_b$ are as defined above.

Preferred examples of C$_2$–C$_{20}$alkylidene are ethylidene, propylidene, butylidene, pentylidene, heptylidene, nonylidene, undecylidene, tridecylidene, pentadecylidene, heptadecylidene and nonadecylidene.

Representative examples of groups containing 1 or 2 C$_5$–C$_7$cycloalkylene groups are cyclohexylene, methylcyclohexylene, cyclohexylenedimethylene, methylenedicyclohexylene and isopropylidenedicyclohexylene.

Representative examples of groups containing 1 or 2 phenylene groups are phenylene, methylphenylene, dimethylphenylene, di-t-butylphenylene, phenylenedimethylene and isopropylidenediphenylene.

If R$_{11}$ is C$_2$–C$_{20}$alkanetriyl, representative examples are ethanetriyl, propanetriyl, butanetriyl or a $$-CH-R_c- \\ | \\ -CH_2$$

group, where R$_c$ is C$_3$–C$_{18}$alkylene.

If R$_{38}$ is C$_3$–C$_{12}$alkanetriyl, preferred examples are 1,2,3-propanetriyl, 1,2,4-butanetriyl, 1,2,6-hexanetriyl or the $$\phantom{R_d-}CH_2- \\ \phantom{R_d-}| \\ R_d-C-CH_2- \\ \phantom{R_d-}| \\ \phantom{R_d-}CH_2-$$

group, where R$_d$ is methyl or ethyl.

If R$_{11}$ is C$_5$–C$_7$cycloalkanetriyl or C$_7$–C$_9$bicycloalkanetriyl, representative examples are the groups.

R$_{38}$ as aliphatic or aromatic triacyl containing not more than 12 carbon atoms is, for example, a triacyl derived from methanetricarboxylic, 1,1,2-ethanetricarboxylic, 1,2,3-propanetricarboxylic, 1,2,3-butanetricarboxylic, citric, 1,2,4-benzenetricarboxylic or 1,3,5-benzenetricarboxylic acids.

If R$_{11}$ is C$_3$–C$_6$alkanetetrayl, representative examples are propanetetrayl, butanetetrayl and pentanetetrayl.

If R$_{46}$ is C$_4$–C$_6$alkanetetrayl, preferred examples are 1,2,3,4-butanetetrayl and the $$\phantom{-CH_2-}CH_2- \\ \phantom{-CH_2-}| \\ -CH_2-C-CH_2- \text{ group.} \\ \phantom{-CH_2-}| \\ \phantom{-CH_2-}CH_2-$$

R$_{46}$, as aliphatic or aromatic tetraacyl containing not more than 12 carbon atoms is, for example, a tetraacyl derived from 1,1,3,3-propanetetracarboxylic, 1,2,3,4-butanetetracarboxylic or 1,2,4,5-benzenetetracarboxylic acids.

Preferred meanings of R$_1$ and R$_{14}$ are hydrogen, C$_1$–C$_4$alkyl, OH, C$_6$–C$_{12}$alkoxy, C$_5$–C$_8$cycloalkoxy, allyl, benzyl or acetyl, in particular hydrogen or methyl.

Preferred compounds of formula (I) are those in which R$_2$ and R$_3$, which may be identical or different, are C$_1$–C$_4$alkyl, C$_1$–C$_4$alkoxy or a group of formula (II), n is 1,2,3 or 4 and, if n is 1, R$_4$ is C$_4$–C$_{28}$alkyl, C$_5$–C$_8$cycloalkyl which is unsubstituted or substituted with 1,2 or 3 C$_1$–C$_4$alkyl, or one of the groups of the formulae (IIIa)–(IIId) in which R$_5$ is C$_4$–C$_{18}$alkyl, C$_4$–C$_{28}$alkyl interrupted by one or more oxygen atoms, C$_5$–C$_8$cycloalkyl which is unsubstituted or substituted with 1,2 or 3 C$_1$–C$_4$alkyl, phenyl which is unsubstituted or substituted with 1,2 or 3 C$_1$–C$_4$alkyl or with C$_1$–C$_4$alkoxy, benzyl which is unsubstituted or substituted on the phenyl with 1,2 or 3 C$_1$–C$_4$alkyl, a group of formula (IV), aliphatic, cycloaliphatic or aromatic acyl containing not more than 20 carbon atoms or an $$R_{15}-N-CO- \\ | \\ R_{16}$$

group, where R$_{15}$ and R$_{16}$, which may be identical or different, are hydrogen, C$_1$–C$_{18}$alkyl, C$_5$–C$_8$cycloalkyl which is unsubstituted or substituted with 1,2 or 3 C$_1$–C$_4$alkyl, benzyl which is unsubstituted or substituted on the phenyl with 1,2 or 3 C$_1$–C$_4$alkyl or a group of formula (IV), or $$R_{15}-N- \\ | \\ R_{16}$$

is 4-morpholinyl or one of the groups of formulae (Va)–(Vc), in which X$_2$ is —CH$_2$CH$_2$— or —CO— or —COCO— and q is zero or 1; R$_6$ is C$_2$–C$_{18}$alkylene; R$_7$ and R$_8$, which may be identical or different, are as defined above for R$_{15}$ and R$_{16}$, or R$_7$ is also (C$_2$–C$_{18}$alkoxy)carbonyl or aliphatic, cycloaliphatic or aromatic acyl containing not more than 20 carbon atoms, or $$R_7-N- \\ | \\ R_8$$

is 4-morpholinyl or one of the groups of formulae (Va)–(Vc) or one of the groups of formulae (VIa)–(VIc) in which X$_3$ is —O— or

where $R_{20}$ is as defined above for $R_{15}$ and $R_{16}$; $R_{17}$ is as defined above for $R_7$ or $R_{17}X_3$— is hydrogen or 4-morpholinyl, $R_{18}$ is hydrogen or methyl and $R_{19}$ is hydrogen or $C_3$–$C_{28}$alkyl; $R_9$ is $C_3$–$C_{18}$alkylene; $R_{10}$ is $C_2$–$C_{18}$ alkyl, $C_5$–$C_8$cycloalkyl which is unsubstituted or substituted with 1,2 or 3 $C_1$–$C_4$alkyl, benzyl which is unsubstituted or substituted on the phenyl with 1,2 or 3 $C_1$–$C_4$alkyl, a group of formula (IV) or a group of formula (VII), $X_1$ is as defined above for $X_3$ or $R_{10}X_1$— is 4-morpholinyl or one of the groups of formulae (Va)–(Vc) or (VIa)–(VIc); p is 1,2 or 3 and, if p is 1, $R_{11}$ is $C_2$–$C_{17}$alkylene and, if p is 2, $R_{11}$ is $C_2$–$C_{20}$alkanetriyl or $C_6$–$C_7$cycloalkanetriyl and, if p is 3, $R_{11}$ is propanetriyl; $R_{12}$ is as defined above for $R_{15}$ and $R_{16}$ and $R_{13}$ is a direct bond or $C_3$–$C_{28}$alkylene; if n is 2, $R_4$ is $C_2$–$C_8$alkylene or $C_4$–$C_{21}$alkylene interrupted by an oxygen atom or by an

group where $R_{21}$ is as defined above for $R_7$, or $R_4$ is one of the groups of formulae (VIIIa)–(VIIIc), in which $X_4$ and $X_5$, which may be identical or different, are —O— or

where $R_{28}$ is as defined above for $R_7$; $R_{22}$ is $C_2$–$C_{18}$alkylene or a $C_rH_{2r}CO$— group, where r is an integer from 2 to 17 and the carbonyl group is bonded to $X_4$ or $X_5$, $R_{23}$ is $C_2$–$C_{10}$alkylene or $C_4$–$C_{10}$alkylene interrupted by 1,2 or 3 oxygen atoms, cyclohexylene, cyclohexylenedimethylene, methylenedicyclohexylene, isopropylidenedicyclohexylene, phenylene, phenylenedimethylene, isopropylidenediphenylene or a group of formula (IXa) or (IXb) in which $R_{29}$ is hydrogen or methyl and $R_{30}$ is $C_2$–$C_{10}$alkylene, $C_4$–$C_{10}$alkylene interrupted by 1,2 or 3 oxygen atoms or phenylenedimethylene or, if $R_{22}$ is $C_2$–$C_{18}$alkylene, $R_{23}$ is also carbonyl or a

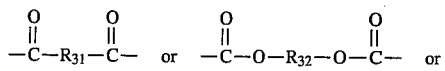

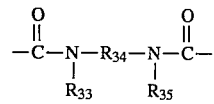

group, where $R_{31}$ is $C_1$–$C_{10}$alkylene, $C_3$–$C_{19}$alkylidene, cyclohexylene or phenylene, $R_{32}$ and $R_{34}$ are $C_2$–$C_{10}$alkylene, $C_4$–$C_{10}$alkylene interrupted by 1,2 or 3 oxygen atoms, cyclohexylene, cyclohexylenedimethylene, methylenedicyclohexylene, isopropylidenedicyclohexylene or a group of formula (IXa) or (IXb) and $R_{33}$ and $R_{35}$, which may be identical or different, are as defined above for $R_{15}$ and $R_{16}$ or the —$R_{23}$—$X_5$ group is a

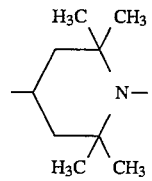

group or the —$X_4$—$R_{23}$—$X_5$— group is a 1,4-piperazinediyl group or a

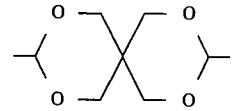

group; $R_{24}$ is $C_3$–$C_{18}$alkylene; $X_6$ and $X_7$, which may be identical or different, are as defined above for $X_4$ and $X_5$, $R_{25}$ is $C_2$–$C_{10}$alkylene, $C_4$–$C_{10}$alkylene interrupted by 1,2 or 3 oxygen atoms, cyclohexylene, cyclohexylenedimethylene, methylenedicyclohexylene, carbonyl or a

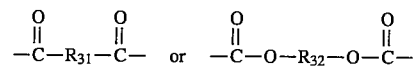

group, with $R_{31}$ and $R_{32}$ as defined above, or the —$X_6$—$R_{25}$—$X_7$— group is an

group, where $R_{36}$ is as defined above for $R_7$; $R_{26}$ is $C_3$–$C_{18}$alkylene or a group of formula (X), where $R_{37}$ is $C_2$–$C_{10}$alkylene, $C_4$–$C_{10}$alkylene interrupted by 1,2 or 3 oxygen atoms, cyclohexylene, cyclohexylenedimethylene or methylenedicyclohexylene and $R_{27}$ is a direct bond or $C_3$–$C_{28}$alkylene; if n is 3, $R_4$ is one of the groups of formulae (XIa)–(XIe), in which $R_{38}$ is $C_3$–$C_{10}$alkanetriyl or aliphatic or aromatic triacyl containing not more than 10 carbon atoms; $R_{39}$ is $C_2$–$C_{18}$alkylene or, if $R_{38}$ is $C_3$–$C_{10}$alkanetriyl, $R_{39}$ is also a —$C_sH_{2s}CO$— group, where s is an integer from 2 to 17 and the carbonyl group is bonded to the oxygen atom; $R_{40}$, $R_{41}$ and $R_{42}$, which may be identical or different, are $C_3$–$C_{18}$alkylene or $R_{40}$ is also a

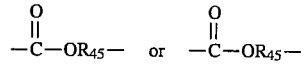

group, where the carbonyl group is bonded to the nitrogen atom and $R_{45}$ is $C_2$–$C_{18}$alkylene; $R_{43}$ is $C_3$–$C_{11}$alkylene and $R_{44}$ is $C_2$–$C_5$alkylene; if n is 4, $R_4$ is one of the groups of formulae (XIIa)–(XIIc) in which $R_{46}$ is $C_4$–$C_6$alkanetetrayl or aliphatic or aromatic tetraacyl containing not more than 10 carbon atoms, $R_{47}$ is $C_2$–$C_{18}$alkylene or, if $R_{46}$ is $C_4$–$C_6$alkanetetrayl, $R_{47}$ is also a —$C_sH_{2s}CO$— group as defined above; $R_{48}$ is $C_3$–$C_{11}$alkylene and $R_{49}$ is as defined above for $R_{25}$.

Particularly preferred compounds of formula (I) are those in which $R_2$ and $R_3$, which may be identical or different, are methyl, ethyl, methoxy, ethoxy or a group of formula (II), n is 1, 2, 3 or 4 and, if n is 1, $R_4$ is $C_6$–$C_{24}$alkyl, cyclohexyl which is unsubstituted or substituted with 1,2 or 3 $C_1$–$C_4$alkyl or one of the groups of formulae (IIIa)–(IIId), in which $R_5$ is $C_6$–$C_{18}$alkyl, $C_6$–$C_{24}$alkyl interrupted by one or more oxygen atoms, cyclohexyl which is unsubstituted or substituted with 1,2 or 3 $C_1$–$C_4$alkyl, benzyl, a group of formula (IV), aliphatic, cycloaliphatic or aromatic acyl containing not more than 18 carbon atoms or an

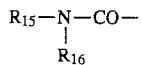

group, where $R_{15}$ and $R_{16}$, which may be identical or different, are $C_1$–$C_{18}$alkyl, cyclohexyl which is unsubstituted or substituted with 1,2 or 3 $C_1$–$C_4$alkyl, benzyl or a group of formula (IV) or

is one of the groups of formulae (Va)–(Vc), in which $X_2$ is —$CH_2CH_2$— or —CO— or —COCO— and q is zero or 1; $R_6$ is $C_2$–$C_{11}$alkylene; $R_7$ and $R_8$, which may be identical or different, are as defined above for $R_{15}$ and $R_{16}$ or hydrogen or $R_7$ is also ($C_4$–$C_{18}$alkoxy)carbonyl or aliphatic, cycloaliphatic aromatic acyl containing not more than 18 carbon atoms, or

is one of the groups of formulae (Va)–(Vc) or one of the groups of formulae (VIa)–(VIc), in which $X_3$ is —O— or

where $R_{20}$ is as defined above for $R_{15}$ and $R_{16}$; $R_{17}$ is as defined above for $R_7$ or $R_{17}X_3$— is hydrogen, $R_{18}$ is hydrogen or methyl and $R_{19}$ is hydrogen or $C_3$–$C_{24}$alkyl; $R_9$ is $C_3$–$C_{11}$alkylene; $R_{10}$ is $C_4$–$C_{18}$alkyl, cyclohexyl which is unsubstituted or substituted with 1,2 or 3 $C_1$–$C_4$alkyl, benzyl, a group of formula (IV) or a group of formula (VII), $X_1$ is as defined above for $X_3$ or $R_{10}X_1$— is one of the groups of formulae (Va)–(Vc) or (VIa)–(VIc); p is 1 or 2 and, if p is 1, $R_{11}$ is $C_2$–$C_{17}$alkylene and, if p is 2, $R_{11}$ is $C_2$–$C_{16}$alkanetriyl; $R_{12}$ is as defined above for $R_{15}$ and $R_{16}$ and $R_{13}$ is a direct bond or $C_3$–$C_{24}$alkylene; if n is 2, $R_4$ is $C_2$–$C_6$alkylene or $C_4$–$C_{14}$alkylene interrupted by an oxygen atom or by an

group, where $R_{21}$ is as defined above for $R_7$ or $R_4$ is one of the groups of formulae (VIIIa)–(VIIIc) in which $X_4$ and $X_5$, which may be identical or different, are —O— or

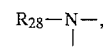

where $R_{28}$ is as defined above for $R_7$; $R_{22}$ is $C_2$–$C_{11}$alkylene or a —$C_rH_{2r}CO$— group, where r is an integer from 2 to 10 and the carbonyl group is bonded to $X_4$ or $X_5$, $R_{23}$ is $C_2$–$C_8$alkylene, $C_4$–$C_{10}$alkylene interrupted by 1,2 or 3 oxygen atoms, cyclohexylene, cyclohexylenedimethylene, methylenedicyclohexylene, phenylene, phenylenedimethylene or a group of formula (IXa), in which $R_{29}$ is hydrogen or methyl or, if $R_{22}$ is $C_2$–$C_{11}$alkylene, $R_{23}$ is also carbonyl, or a

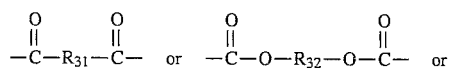

group, where $R_{31}$ is $C_2$–$C_8$alkylene, $C_5$–$C_{13}$alkylidene, cyclohexylene or phenylene, $R_{32}$ and $R_{34}$ are $C_2$–$C_8$alkylene, $C_4$–$C_{10}$alkylene interrupted by 1,2 or 3 oxygen atoms, cyclohexylene, cyclohexylenedimethylene, methylenedicyclohexylene or a group of formula (IXa) and $R_{33}$ and $R_{35}$, which may be identical or different, are as defined above for $R_{15}$ and $R_{16}$ or the —$R_{23}$—$X_5$— group is a

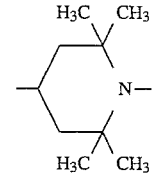

group; $R_{24}$ is $C_3$–$C_{11}$alkylene; $X_6$ and $X_7$, which may be identical or different, are as defined above for $X_4$ and $X_5$, $R_{25}$ is $C_2$–$C_8$alkylene, $C_4$–$C_{10}$alkylene interrupted by 1,2 or 3 oxygen atoms, cyclohexylene, cyclohexylenedimethylene, methylenedicyclohexylene, carbonyl or a

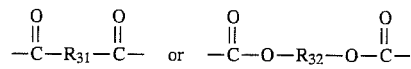

group, with $R_{31}$ and $R_{32}$ as defined above, or the group —$X_6$—$R_{25}$—$X_7$— is an

group, where $R_{36}$ is as defined above for $R_7$, $R_{26}$ is $C_3$–$C_{11}$alkylene or a group of formula (X), where $R_{37}$ is $C_2$–$C_8$alkylene, $C_4$–$C_{10}$alkylene interrupted by 1,2 or 3 oxygen atoms, cyclohexylene, cyclohexylenedimethylene or methylenedicyclohexylene and $R_{27}$ is a direct bond or $C_3$–$C_{24}$alkylene; if n is 3, $R_4$ is one of the groups of formulae (XIa)–(XIe), in which $R_{38}$ is $C_3$–$C_8$alkanetriyl or aliphatic $C_4$–$C_7$triacyl; $R_{39}$ is $C_2$–$C_{11}$alkylene or, if $R_{38}$ is $C_3$–$C_8$alkanetriyl, $R_{39}$ is also a —$C_sH_{2s}CO$— group, where s is an integer from 2 to 10 and the carbonyl group is bonded to the oxygen atom, $R_{40}$, $R_{41}$ and $R_{42}$, which may be identical or different, are
$C_3$-$C_{11}$alkylene or $R_{40}$ is also a

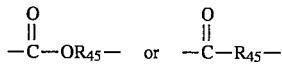

group, where the carbonyl group is bonded to the nitrogen atom and $R_{45}$ is $C_2$-$C_{11}$alkylene, $R_{43}$ is $C_3$-$C_6$alkylene and $R_{44}$ is $C_2$-$C_4$alkylene; if n is 4, $R_4$ is one of the groups of formulae (XIIa)–(XIIc) in which $R_{46}$ is $C_4$-$C_5$alkanetetrayl or aliphatic $C_6$-$C_8$tetraacyl, $R_{47}$ is $C_2$-$C_{11}$alkylene or, if $R_{46}$ is $C_4$-$C_5$alkanetetrayl, $R_{47}$ is also a —$C_sH_{2s}CO$— group as defined above; $R_{48}$ is $C_3$-$C_6$alkylene and $R_{49}$ is as defined above for $R_{25}$.

Compounds of formula (I) of special interest are those in which $R_2$ and $R_3$, which may be identical or different, are methyl, methoxy, ethoxy or a group of formula (II), n is 1,2,3 or 4 and, if n is 1, $R_4$ is $C_8$-$C_{20}$alkyl, cyclohexyl or one of the groups of formulae (IIIa)–(IIId) in which $R_5$ is $C_8$-$C_{18}$alkyl, $C_{10}$-$C_{22}$alkyl interrupted by 1 or 2 oxygen atoms, cyclohexyl, benzyl, a group of formula (IV), aliphatic $C_8$-$C_{18}$acyl or an

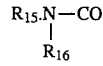

group, where $R_{15}$ and $R_{16}$, which may be identical or different, are $C_4$-$C_{18}$alkyl, cyclohexyl, benzyl or a group of formula (IV), or

is one of the groups of formulae (Va)–(Vc), in which $X_2$ is —$CH_2CH_2$—, —CO— or —COCO— and q is zero or 1; $R_6$ is $C_2$-$C_5$alkylene; $R_7$ and $R_8$, which may be identical or different, are as defined above for $R_{15}$ and $R_{16}$ or are hydrogen, or $R_7$ is also ($C_8$-$C_{18}$alkoxy)carbonyl or aliphatic $C_8$-$C_{18}$acyl or

is one of the groups of formulae (Va)–(Vc) or one of the groups of formulae (VIa)–(VIc), in which $X_3$ is —O— or

where $R_{20}$ is as defined above for $R_{15}$ and $R_{16}$; $R_{17}$ is as defined above for $R_7$, $R_{18}$ is hydrogen and $R_{19}$ is $C_8$-$C_{18}$alkyl; $R_9$ is $C_3$-$C_5$alkylene; $R_{10}$ is $C_8$-$C_{18}$alkyl, cyclohexyl, benzyl, a group of formula (IV) or a group of formula (VII), $X_1$ is as described above for $X_3$ or $R_{10}X_1$— is one of the groups of formulae (Va)–(Vc) or (VIa)–(VIc); p is 1 or 2 and, if p is 1, $R_{11}$ is $C_2$-$C_{10}$alkylene and, if p is 2, $R_{11}$ is $C_2$-$C_{14}$alkanetriyl; $R_{12}$ is as defined above for $R_{15}$ and $R_{16}$ and $R_{13}$ is a direct bond or $C_3$-$C_{18}$alkylene; if n is 2, $R_4$ is $C_2$-$C_4$alkylene, $C_4$-$C_{14}$alkylene interrupted by an oxygen atom or $C_6$-$C_{10}$alkylene interrupted by an

group, where $R_{21}$ is as defined above for $R_7$, or $R_4$ is one of the groups of formulae (VIIIa)–(VIIIc), in which $X_4$ and $X_5$, which may be identical or different, are —O— or

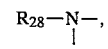

where $R_{28}$ is as defined above for $R_7$; $R_{22}$ is $C_2$-$C_5$alkylene or a —$C_rH_{2r}CO$— group, where r is an integer from 2 to 10 and the carbonyl group is bonded to $X_4$ or $X_5$, $R_{23}$ is $C_2$-$C_6$alkylene, $C_6$-$C_{10}$alkylene interrupted by 2 or 3 oxygen atoms, cyclohexylenedimethylene, methylenedicyclohexylene or a group of formula (IXa), in which $R_{29}$ is hydrogen or, if $R_{22}$ is $C_2$-$C_5$alkylene, $R_{23}$ is also carbonyl

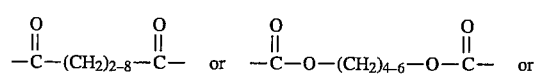

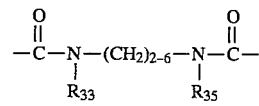

group, where $R_{33}$ and $R_{35}$ are a group of formula (IV), or the —$R_{23}$–$X_5$ group is a

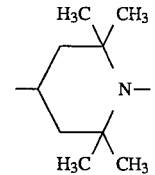

group; $R_{24}$ is $C_3$-$C_5$alkylene; $X_6$ and $X_7$ are as defined above for $X_4$ and $X_5$; $R_{25}$ is $C_2$-$C_6$alkylene, $C_6$-$C_{10}$alkylene interrupted by 2 or 3 oxygen atoms, cyclohexylenedimethylene, methylenedicyclohexylene or a

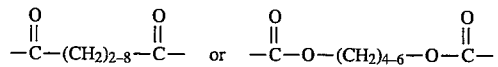

group; $R_{26}$ is $C_3$-$C_5$alkylene or a group of formula (X), where $R_{37}$ is $C_2$-$C_{10}$alkylene, $C_6$-$C_{10}$ alkylene interrupted by 2 or 3 oxygen atoms, cyclohexylenedimethylene or methylenedicyclohexylene and $R_{27}$ is a direct bond or $C_3$-$C_{18}$alkylene; if n is 3, $R_4$ is one of the groups of formulae (XIa)–(XIe), in which $R_{38}$ is $C_3$-$C_6$alkanetriyl or aliphatic $C_5$-$C_7$triacyl; $R_{39}$ is $C_2$-$C_5$alkylene or, if $R_{38}$ is $C_3$-$C_6$alkanetriyl, $R_{39}$ is also a —$C_sH_{2s}CO$— group, where s is an integer from 2 to 10 and the carbonyl group is bonded to the oxygen atom; $R_{40}$, $R_{41}$ and $R_{42}$, which may be identical or different, are $C_3$-$C_5$alkylene, or $R_{40}$ is also a

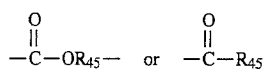

group, where the carbonyl group is bonded to the nitrogen atom and $R_{45}$ is $C_2$–$C_{11}$alkylene; $R_{43}$ is $C_3$–$C_5$alkylene and $R_{44}$ is $C_2$–$C_4$alkylene; if n is 4, $R_4$ is one of the groups of formulae (XIIa)–(XIIc), in which $R_{46}$ is a

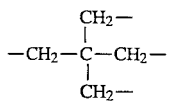

group, $R_{47}$ is $C_2$–$C_5$alkylene; $R_{48}$ is $C_3$–$C_5$alkylene and $R_{49}$ is as defined above for $R_{25}$.

Compounds of formula (I) of particular interest are those in which $R_1$ and $R_{14}$ are hydrogen or methyl, $R_2$ and $R_3$, which may be identical or different, are methyl or a group of formula (II), n is 1,2,3, or 4 and, if n is 1, $R_4$ is $C_{12}$–$C_{18}$alkyl or one of the groups of formulae (IIIa)–(IIId) in which $R_5$ is $C_{12}$–$C_{18}$alkyl, a group of formula (IV), aliphatic $C_{12}$–$C_{18}$acyl or an

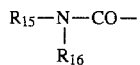

group, where $R_{15}$ and $R_{16}$, which may be identical or different, are $C_4$–$C_{12}$alkyl or a group of formula (IV), $R_6$ is ethylene or trimethylene, $R_7$ and $R_8$, which may be identical or different, are as defined above for $R_{15}$ or $R_{16}$ or hydrogen, or

is a group of formula (Va), in which $X_2$ is —$CH_2CH_2$— or —CO— and q is zero or 1, or a group of formula (VIb) in which $R_{18}$ is hydrogen, $R_9$ is trimethylene, $R_{10}$ is a group of formula (IV), $X_1$ is —O— or —NH—, p is 1 or 2 and, if p is 1, $R_{11}$ is $C_2$–$C_{10}$alkylene and, if p is 2, $R_{11}$ is $C_2$–$C_4$alkanetriyl, $R_{12}$ is $C_{12}$–$C_{18}$alkyl and $R_{13}$ is a direct bond; if n is 2, $R_4$ is a

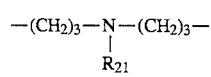

group, where $R_{21}$ is $C_{12}$–$C_{18}$alkyl, ($C_{12}$–$C_{18}$alkoxy)carbonyl or aliphatic $C_{12}$–$C_{18}$acyl, or $R_4$ is one of the groups of formulae (VIII)–(VIIIc), in which $X_4$ and $X_5$ are

where $R_{28}$ is a group of formula (IV), $R_{22}$ is trimethylene or a —$CH_2CH_2CO$— group, with the carbonyl group bonded to $X_4$ or $X_5$, $R_{23}$ is —$(CH_2)_{2-6}$—, $R_{24}$ is trimethylene, $X_6$ and $X_7$ are —O—, $R_{25}$ is

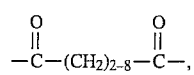

$R_{26}$ is a group of formula (X), in which $R_{37}$ is —$(CH_2)_{2-6}$— and $R_{27}$ is a direct bond; if n is 3, $R_4$ is one of the groups of formulae (XIa)–(XIe), in which $R_{38}$ is a

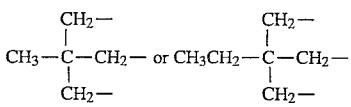

—$CH_2CH_2CO$— group, with the carbonyl group bonded to the oxygen atom and $R_{40}$, $R_{41}$, $R_{42}$, $R_{43}$ and $R_{44}$ are trimethylene; if n is 4, $R_4$ is one of the groups of formulae (XIIa)–(XIIc), in which $R_{46}$ is a

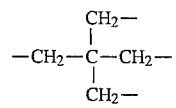

group, $R_{47}$ is $C_2$–$C_5$alkylene; $R_{48}$ is $C_3$–$C_5$alkylene and $R_{49}$ is as defined above for $R_{25}$.

The compounds of the present invention can be prepared in accordance with various processes known per se.

According to process A, the compounds of the formula (I) can be prepared by reacting, in the appropriate molar ratios and in the presence of a transesterification catalyst, a compound of formula (XIII)

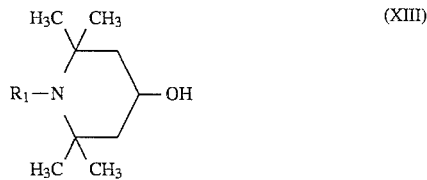

with a compound of formula (XIV)

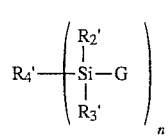

where n is as defined above, G is $C_1$–$C_8$alkoxy, $R_2'$ and $R_3'$, which may be identical or different, are $C_1$–$C_8$alkyl, phenyl or $C_1$–$C_8$alkoxy and $R_4'$ is as defined above for $R_4$, except that, when $R_{10}$ is a group of formula (VII), the said group is replaced by the group of formula (VII')

The reaction is carried out without a solvent or in an inert organic solvent, for example benzene, toluene, xylene, mesitylene, cyclohexane, heptane, octane, tetrahydrofuran or dioxane, at a temperature of between 65° and 200° C., preferably between 100° and 180° C.

As the transesterification catalyst there may for example be used an alkali metal, a $C_1$–$C_4$alkoxide or amide or hydride of an alkali metal, a $C_1$–$C_4$ alkoxide of Ti(IV) or dibutyltin oxide.

If $R_4$ is a group of formula (IIIc), in which $X_1$ is —O— and $R_{10}$ is different from a group of formula (IV), it is possible that, in the same reaction, the said group $R_{10}$ can also be replaced by a group of formula (IV).

According to process B, the compounds of formula (I) can be prepared by reacting, in the appropriate molar ratios and in the presence of an organic base, a compound of formula (XIII) with a compound of formula (XV)

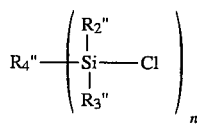
(XV)

where n is as defined above, $R_2"$ and $R_3"$, which may be identical or different, are $C_1$–$C_8$alkyl, phenyl or Cl and $R_4"$ is as defined above for $R_4$, except that, if $R_{10}$ is a group of formula (VII), the said group is replaced by the group of formula (VII")

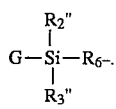
(VII')

The reaction is carried out in an inert organic solvent, for example one of the solvents mentioned above, at a temperature of between 0° and 150° C., preferably between 20° and 120° C.

As the organic base there may for example be employed methylamine or tributylamine or pyridine, in an amount at least equivalent to the hydrochloric acid liberated during the reaction.

An excess of the organic base can also be employed as the solvent. As an alternative to the said organic bases, it is possible to employ the compounds of formula (XIII) in the form of alcoholates of alkali metals, in particular of sodium or potassium.

According to process C, the compounds of formula (I) can be prepared by reacting, in the appropriate molar ratios and in the presence of a hydrosilylation catalyst, a compound of formula (XVI)

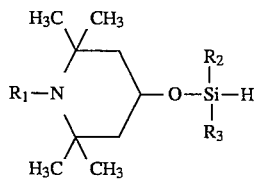

with an alkene capable of forming the group $R_4$.

The reaction is carried out in an inert organic solvent, for example one of the solvents mentioned above, at a temperature of between 50° and 150° C., preferably between 80° and 130° C.

As a hydrosilylation catalyst there may be employed, for example, Pd, Pt, Rh or their derivatives, preferably complexes of Pt and Rh, in particular $H_2PtCl_6$, the $PtCl_2(Ph—CH=CH_2)_2$ complex and the $PtCl_2(dimethyl\ sulfoxide)_2$ complex.

The reaction can be carried out without a solvent or in an inert organic solvent, for example one of the solvents mentioned above, at a temperature of between 50° and 150° C., preferably between 80° and 130° C.

The intermediate compounds of formula (XIV) and (XV), respectively, and can be prepared by hydrosilylation of an alkene capable of forming the group $R_4$, and with a silane of formula

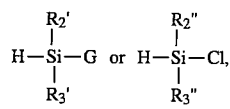

in the presence of a hydrosilylation catalyst, in accordance with process C.

The intermediate compounds of formula (XVI) can be prepared by reacting a compound of formula (XIII) with a silane of formula

in the presence of a transesterification catalyst, in accordance with process A.

The compounds of formula (XIII) and the other intermediates are commercially available or can be prepared in accordance with known processes.

As pointed out initially, the compounds of formula (I) are very effective in improving the light resistance, heat resistance and oxidation resistance of organic materials, in particular synthetic polymers and copolymers.

Examples of such organic materials which can be stabilised are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of formula (I) are particularly suitable for improving the light stability, heat stability and stability to oxidation of polyolefins, particularly polyethylene and polypropylene.

The compounds of the formula (I) are especially suitable for the light stabilization of polypropylene thick sections.

The compounds of formula (I) can be used in mixtures with organic materials in various proportions depending on the nature of the material to be stabilised, on the end use and on the presence of other additives.

In general, it is appropriate to use, for example, 0.01 to 5% by weight of the compounds of formula (I), relative to the weight of the material to be stabilised, preferably between 0.05 and 1%.

In general, the compounds of formula (I) can be incorporated in the polymeric materials before, during or after the polymerisation or crosslinking of the said materials.

The compounds of formula (I) can be incorporated in the polymeric materials in the pure form or encapsulated in waxes, oils or polymers.

The compounds of formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of formula (I) can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flameproofing agents, lubricants, corrosion inhibitors and metal deactivators, can be added to the mixtures of the compounds of formula (I) with the organic materials.

Particular examples of additives which can be used in admixture with the compounds of formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)- 4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl- 6-(1'-methylundec-1'-yl)phenol, 2,4-dimethyl-6-( 1'-methylheptadec-1'-yl)phenol, 2,4-dimethyl-6-( 1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4methoxyphenol, 2,5-di-tert-butylhydroquinone, 2,5-di-tert-amylhydroquinone, 2,6-diphenyl-4-octadecyloxyphenol, 2,6-di-ten-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-( 2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-($\alpha$-methylbenzyl)-4-nonylphenol], 2,2'-methylenebis[6-($\alpha,\alpha$-dimethylbenzyl)-4-nonylphenol], 4,4'-methylenebis(2, 6-di-tert-butylphenol), 4,4'-methylenebis( 6-tert-butyl-2-methylphenol), 1,1-bis(5-tert-butyl-4-hydroxy-2-methylphenyl)butane, 2,6-bis( 3-tert-butyl-5-methyl-2-hydroxybenzyl)-4-methylphenol, 1,1,3-tris( 5-tert-butyl-4-hydroxy2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis( 3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2hydroxyphenyl)butane, 2,2-bis-(3,5-di-tert-butyl-4-hydroxyphenyl)propane, 2,2-bis-( 5-tert-butyl-4-hydroxy2-methylphenyl)-4-n-dodecylmercaptobutane, 1,1, 5,5-tetra-( 5-tert-butyl-4-hydroxy2-methylphenyl)pentane.

1.6. O—, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-( 3,5-di-tert-butyl-4-hydroxybenzyl)amine, bis( 4-tert-butyl-3-hydroxy-2,6-dimethylbenzyl)dithioterephthalate, bis(3,5- di-tert-butyl-4-hydroxybenzyl)sulfide, isooctyl-3,5-di-tert-butyl-4-hydroxybenzylmercaptoacetate.

1.7. Hydroxybenzylated malonates, for example dioctadecyl-2,2-bis-(3,5-di-tert-butyl- 2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl- 4-hydroxybenzyl)-2,4,6-trimethylbenzene, 1,4-bis(3,5-di-tert-butyl-4-hydroxybenzyl)-2,3,5,6tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl- 4-hydroxyanilino)-1,3,5-triazine, 2-octylmercapto-4,6-bis(3,5-di-tert-butyl- 4-hydroxyanilino)-1,3,5-triazine, 2-octylmercapto-4,6-bis(3,5-di-tert-butyl-4-hydroxyphenoxy)1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy- 2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl 3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1 -phospha-2,6,7-trioxabicyclo[2.2.2]octane.

1.14 Esters of β-(3,5-dicyclohexyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Amides of β-(3,5-di-tert-butyl-4-hydroxyphenyl)propionic acid e.g. N,N'-bis( 3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl- 4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole,2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-( 3'-tert-butyl-2'-hydroxy-5'-methylphenyl)- 5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-( 3',5'-di-tert-amyl-2'-hydroxyphenyl)benzotriazole, 2-(3',5'-bis-(α,α-dimethylbenzyl)- 2'-hydroxyphenyl)benzotriazole, mixture of 2-(3'-tert-butyl-2'-hydroxy-5'-( 2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-( 3'-tert-butyl-2'-hydroxy-5'-( 2-methoxycarbonylethyl)phenyl)benzotriazole, 2-(3'-tert-butyl-2'-hydroxy- 5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO($CH_2$)—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert-butylphenyl salicylate, phenyl salicylate, octylphenyl salicylate, dibenzoyl resorcinol, bis( 4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6tetramethylpiperidine, 4-stearyloxy-2,2,6,6-tetramethylpiperidine, bis( 1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy- 2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis( 4-n-butyl-amino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl- 7,7,9,9-tetramethyl-1,3,8-triazaspiro[4.5]decane-2,4-dione, 3-dodecyl-1-(2,2,6,6-tetramethyl- 4piperidyl)pyrrolidin-2,5-dione, 3-dodecyl-1-(1,2,2,6,6-pentamethyl- 4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and parametoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy- 4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-( 2-hydroxy-4-octyloxyphenyl)-4,6-bis(4-methylphenyl)-1,3,5-triazine, 2-(2-hydroxy- 4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-( 2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetratert-butyl-12H-dibenz[d,g]-1,3,2-dioxaphosphocin, 6-fluoro- 2,4,8,10-tetra-tert-butyl-12-methyl-dibenz[d,g]-1, 3,2-dioxaphosphocin, bis(2,4-di-tert-butyl- 6methylphenyl)methylphosphite, bis(2,4-di-tert-butyl-6-methylphenyl)ethylphosphite.

4bis. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244 or U.S. Pat. No. 5,175,312, or 3-[4-(2-acetoxyethoxy)phenyl]- 5,7-di-tert-butyl-benzofuran-2-one 5,7-di-tert-butyl-3-[4-(2-stearoyloxyethoxy)phenyl]benzofuran- 2-one, 3,3'-bis[5,7-di-tert-butyl- 3-(4-[2-hydroxyethoxy]phenyl)benzofuran-2-one], 5,7-di-tert-butyl-3-(4-ethoxyphenyl )benzofuran-2-one, 3-(4-acetoxy-3,5-dimethylphenyl )- 5,7-di-tert-butylbenzofuran-2-one, 3-(3,5-dimethyl-4-pivaloyloxyphenyl)-5,7-di-tert-butyl-benzofuran-2-one.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

In order to illustrate the present invention more clearly, there will now be described some examples of the preparation and of the use of the compounds of formula (I); these examples are given purely by way of illustration and do not imply any limitation.

EXAMPLE 1

Preparation of the compound of formula

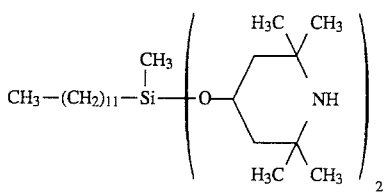

A mixture of 30 g (99.2 mmols) of dodecyldiethoxymethylsilane, 34.3 g (218 mmols) of 2,2,6,6-tetramethyl-4-piperidinol and 1.4 ml of Ti(IV) isopropoxide in 120 ml of toluene is heated to a refluxing temperature for 6 hours, with removal of the ethanol formed. Thereafter, the mixture is heated for a further 2 hours, whilst distilling off 60 ml of toluene.

After cooling to ambient temperature, the reaction mixture is diluted with 30 ml of toluene, washed with water, dried over anhydrous $Na_2SO_4$ and evaporated under reduced pressure. The residue is distilled in vacuo: a colourless oil of boiling point 236°–238° C./1.5 mbar is obtained.

Analysis for $C_{31}H_{64}N_2O_2Si$ Calculated: C=70.93%; H=12.29%; N=5.34% Found: C=70.73%; H=12.28%; N=5.35%

EXAMPLE 2

The same compound as in Example 1 is prepared by adding 15 g (53 mmols) of dichlorododecylmethylsilane to a solution of 18.4 g (117 mmols) of 2,2,6,6-tetramethyl-4-piperidinol in 80 ml of triethylamine and heating to the reflux temperature for 1 hour.

After cooling to ambient temperature, the precipitate formed is filtered off, the excess triethylamine is evaporated and the residue is purified by distillation in vacuo, giving the desired product as a colourless oil with boiling point 236°–238° C./1.5 mbar.

Analysis for $C_{31}H_{64}N_2O_2Si$ Calculated: C=70.93%; H=12.29%; N=5.34% Found: C=70.82%; H=12.27%; N=5.33%

EXAMPLE 3

Following the process described in Example 1, 19.9 g (60 mmols) of 4-[3-(diethoxymethylsilyl)propoxy]-2,2,6,6-tetramethylpiperidine are caused to react with 20.8 g (132 mmols) of 2,2,6,6-tetramethyl-4-piperidinol in 100 ml of xylene in the presence of 1.5 ml of Ti(IV) isopropoxide.

After distillation, the compound of formula

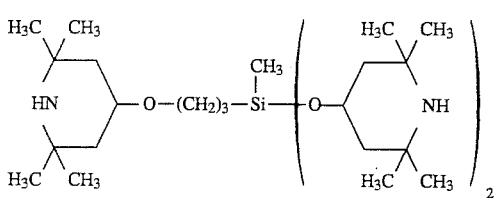

is obtained as a colourless oil of boiling point 195°–197° C./0.06 mbar.

Analysis for $C_{31}H_{63}N_3O_3Si$ Calculated: C=67.22%; H=11.46%; N=7.59% Found: C=66.94%; H=11.43%; N=7.54%

EXAMPLE 4

Following the process described in Example 1,100.2 g (290 mmols) of 4-[3-(diethoxymethylsilyl)propoxy]-1,2,2,6,6-pentamethylpiperidine are caused to react with 109.3 g (638 mmols) of 1,2,2,6,6-pentamethyl-4-piperidinol in 300 ml of xylene in the presence of 2.5 ml of Ti(IV) isopropoxide.

After distillation, the compound of formula

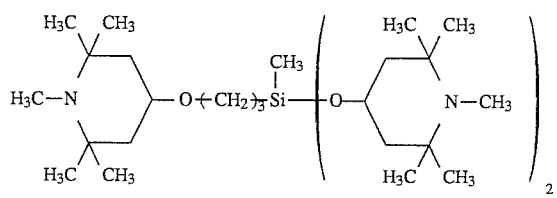

is obtained as a colourless oil of boiling point 191°–193° C./0.5 mbar. Analysis for $C_{34}H_{69}N_3O_3Si$ Calculated: C=68.52%; H=11.67%; N=7.05% Found: C=68.11%; H=11.65%; N=7.06%

EXAMPLE 5

Following the process described in Example 1, 40 g (92.9 mmols) of 3-(diethoxymethylsilyl)propylbutyl(2,2,6,6-tetramethyl-4-piperidyl)carbamate are reacted with 32.1 g (204.3 mmols) of 2,2,6,6-tetramethyl-4-piperidinol in 120 ml of toluene in the presence of 2 ml of Ti(IV) isopropoxide.

After distillation, the compound of formula

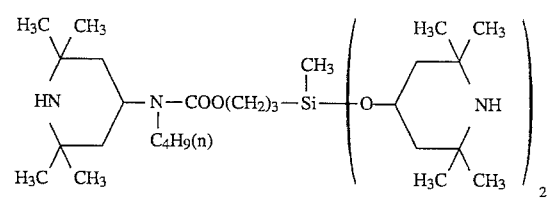

is obtained as a colourless oil of boiling point 249°–251° C./0.02 mbar.

Analysis for $C_{36}H_{72}N_4O_4Si$ Calculated: C=66.21%; H=11.11%; N=8.58% Found: C=66.07%; H=11.10%; N=8.51%

EXAMPLE 6

Following the process described in Example 1, 20 g (90.3 mmols) of 3-(triethoxysilyl)propanamine are reacted with 46.9 g (298 mmols) of 2,2,6,6-tetramethyl-4-piperidinol in 120 ml of toluene in the presence of 2 ml of Ti(IV) isopropoxide.

After distillation, the compound of formula

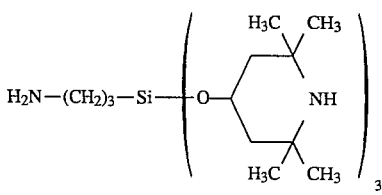

is obtained as a colourless oil of boiling point 175°–177° C./0.05 mbar.

Analysis for $C_{30}H_{62}N_4O_3Si$ Calculated: C =64.93%; H=11.26%; N=10.10% Found: C=64.87%; H=11.28%; N=10.07%

EXAMPLE 7

Following the process described in Example 1, 30 g (75 mmols) of 3-[3-(diethoxymethylsilyl)propyl]-7,7,9,9-tetramethyl-1,3,8-triazaspiro[4.5]decane-2,4-dione are reacted with 26 g (165 mmols) of 2,2,6,6-tetramethyl-4-piperidinol in 120 ml of toluene in the presence of 1.5 ml of Ti(IV) isopropoxide.

After crystallisation from n-hexane, the compound of formula

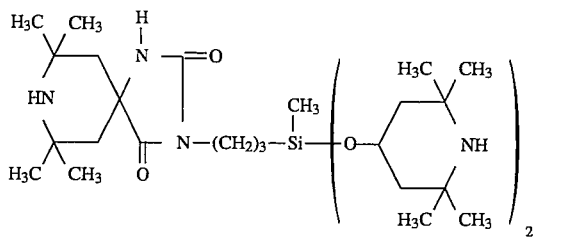

is obtained as a white powder melting at 50°–52° C.

Analysis for $C_{33}H_{63}N_5O_4Si$ Calculated: C=63.73%; H=10.21%; N=11.26% Found: C=63.18%; H=10.06%; N=11.20%

EXAMPLE 8

Following the process described in Example 1, 41.6 g (120 mmols) of ethyl 11-(diethoxymethylsilyl)undecanoate are reacted with 62.3 g (396 mmols) of 2,2,6,6-tetramethyl-4-piperidinol in 180 ml of xylene in the presence of 2.5 ml of Ti(IV) isopropoxide.

After distillation of the excess 2,2,6,6-tetramethyl-piperidinol, the residue is taken up in toluene and the mixture is washed with water.

After separating off the organic phase and evaporating it at 80° C. in vacuo (1.3 mbar), the compound of formula

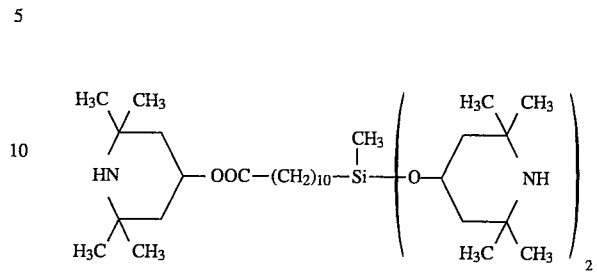

is obtained as a very dense colourless oil.

Analysis for $C_{39}H_{77}N_3O_4Si$ Calculated: C=68.87%; H=11.41%; N=6.18% Found: C=68.87%; H=11.40%; N=6.14%

EXAMPLE 9

Following the process described in Example 1, 41.6 g (120 mmols) of ethyl 11-(diethoxymethylsilyl)undecanoate are caused to react with 67.8 g (396 mmols) of 1,2,2,6,6-pentamethyl-4-piperidinol in 180 ml of xylene in the presence of 2.5 ml of Ti(IV) isopropoxide.

After distillation of the excess 1,2,2,6,6-pentamethyl-4-piperidinol, the compound of the formula

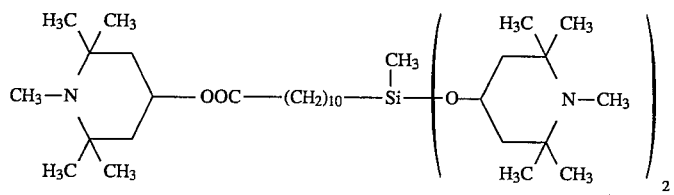

is obtained as a colourless viscous oil.

Analysis for $C_{42}H_{83}N_3O_4Si$ Calculated: C=69.85%; H=11.58%; N=5.82% Found: C-69.36%; H=11.52%; N=5.79%

EXAMPLE 10

Following the process described in Example 1, 40 g (87.6 mmols) of 11-(diethoxymethylsilyl)-N-(2,2,6,6-tetramethyl-4-piperidyl)undecanamide are caused to react with 30.3 g (192.6 mmols) of 2,2,6,6-tetramethyl-4-piperidinol in 120 ml of toluene in the presence of 1.5 ml of Ti(IV) isopropoxide.

After distillation, the compound of formula

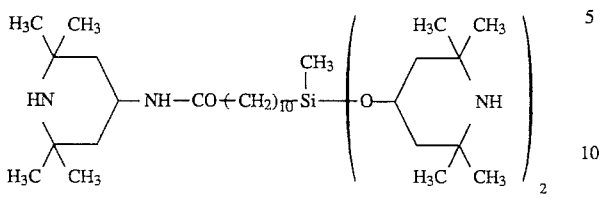

is obtained as a straw-coloured oil of boiling point 278°–280° C./0.01 mbar.

Analysis for $C_{39}H_{78}N_4O_3Si$ Calculated: C=68.97%; H=11.58%; N=8.25% Found: C=69.00%; H=11.61%; N=8.21%

EXAMPLE 11

Following the process described in Example 1, 16.7 g (50 mmols) of diethyl [3-(diethoxymethylsilyl)propyl]malonate are caused to react with 34.6 g (220 mmols) of 2,2,6,6-tetramethyl-4-piperidinol in 150 ml of mesitylene in the presence of 2 ml of Ti(IV) isopropoxide.

After purification by column chromatography over silica gel (eluant: tetrahydrofuran), a compound of formula

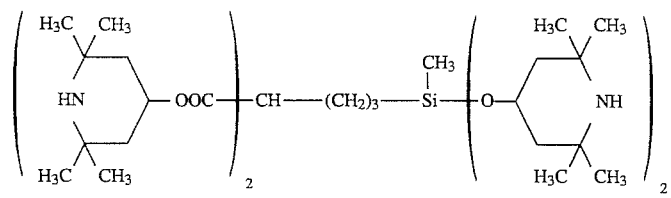

is obtained as a dense straw-coloured oil.

Analysis for $C_{43}H_{82}N_4O_6Si$ Calculated: C=66.28%; H=10.61%; N=7.19% Found: C=65.77%; H=10.57%; N=7.14%

EXAMPLE 12

Following the process described in Example 1, 40 g (53.8 mmols) of N,N'-bis[3-(diethoxymethylsilyl)propyl]-N,N'-bis(2,2,6,6-tetramethyl-4-piperidyl)-1,6-hexanediamine are caused to react with 37.2 g (236.7 mmols) of 2,2,6,6-tetramethyl-4-piperidinol in 150 ml of toluene in the presence of 2 ml of Ti(IV) isopropoxide.

After purification by column chromatography using silica gel (eluant: a 2/1 mixture of tetrahydrofuran and methanol), the compound of formula

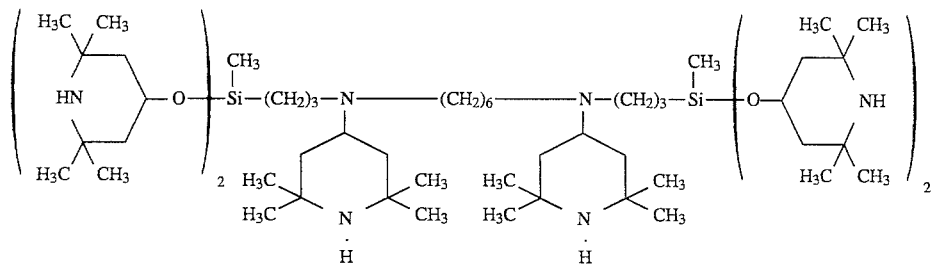

is obtained as a resin of pale yellow colour.

Analysis for $C_{68}H_{138}N_8O_4Si_2$ Calculated: C=68.75%; H=11.71%; N=9.43% Found: C=68.60%; H=11.59%; N=9.36%

EXAMPLE 13

Following the process 1described in Example 1, 23.2 g (60 mmol) of octadecyl diethyloxy methyl silane are caused to react with 20.8 g (132 mmol) of 2,2,6,6-tetramethyl-4-piperidinol in 100ml of xylene in the presence of 1.5 ml of Ti (IV)isopropoxide.

After distillation of the excess of the alcohol the residue is taken up in toluene and the mixture is washed with water. After separating off the organic phase and evaporating it at 80° C. in vacuo (1.3 mbar), the compound of the formula

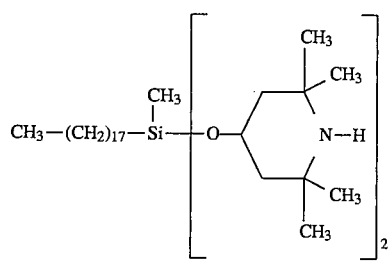

is obtained as a white solid with m.p. 38°–40 ° C.

Analysis for $C_{37}H_{76}N_2O_2Si$ Calculated: C=72.96%; H=12.58%; N=4.60% Found: C=72.35%; H=12.57%; N=4.58%

EXAMPLE 14

Following the process described in Example 1, 30 g (99.2 mmol) of dodecyldiethoxy methyl silane are caused to react with 37.3 g (218 mmol) of 1,2,2,6,6-pentamethyl-4-piperidinol in 120 ml of xylene in the presence of 1.7 ml of Ti(IV)isopropoxide.

After distillation the compound of the formula

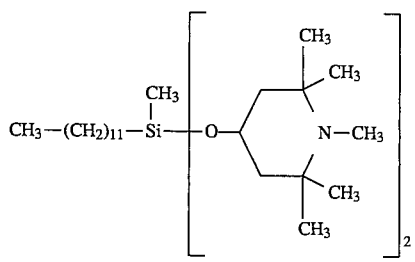

is obtained as a colourless oil of boiling point 228° C./1 mbar.

Analysis for $C_{33}H_{68}N_2O_2Si$ Calculated: C=71.67%; H=12.39%; N=5.07% Found: C=71.05%; H=12.34%; N=5.06%

EXAMPLE 15

Following the process described in Example 1, 21.7 g (60 mmol) of 4(3-triethoxysilyl propoxy)-2,2,6,6-tetramethyl piperidine are caused to react with 31.13 g (198 mmol) of 2,2,6,6-tetramethyl-4-piperidinol in 130 ml of xylene in the presence of 2.0 ml of Ti(IV)isopropoxide.

After distillation the compound of the formula

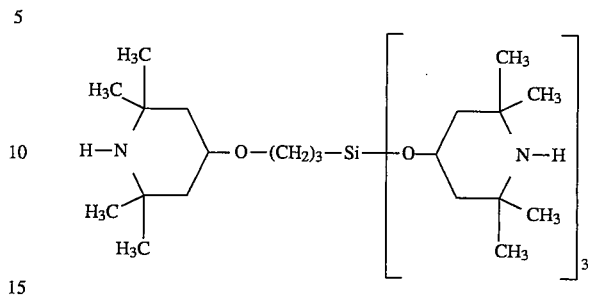

is obtained as a colourless oil of boiling point 230° C./0.01 mbar.

Analysis for $C_{39}H_{78}N_4O_4Si$ Calculated: C=67.38%; H=11.31%; N=8.06% Found: C=67.31%; H=11.25%; N=8.00%

EXAMPLE 16

Following the process described in Example 1, 45.2 g (120 mmol) of ethyl 11 (triethoxysilyl) undecanoate are caused to react with 83.0 g (528 mmol) of 2,2,6,6-tetramethyl-4-piperidinol in 200 ml of xylene in the presence of 3.0 ml of Ti(IV)isopropoxide.

After distillation of the excess of 2,2,6,6-tetramethyl-4-piperidinol the residue is taken up in toluene and the mixture is washed with water. After separating off the organic phase and evaporating it at 80° C. in vacuo (1.3 mbar), the compound of the formula

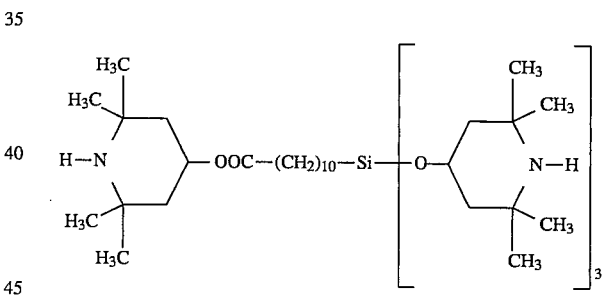

is obtained as a very dense colourless oil.

Analysis for $C_{47}H_{92}N_4O_5Si$ Calculated: C=68.73%; H=11.29%; N=6.82% Found: C=68.74%; H=11.30%; N=6.82%

EXAMPLE 17

Following the process described in Example 1, 33.3 g (100 mmol) of dodecyl triethoxy silane are caused to react with 51.9 g (330 mmol) of 2,2,6,6-tetramethyl-4-piperidinol in 150 ml of xylene in the presence of 2.5 ml of Ti(IV) isopropoxide.

After distillation the compound of the formula

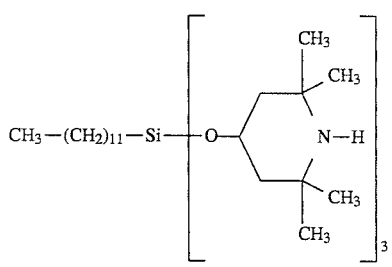

is obtained as a colourless oil of boiling point 194° C./0.01 mbar.

Analysis for $C_{39}H_{79}N_3O_3Si$ Calculated: C=70.32%; H=11.95%; N=6.31% Found: C=70.31%; H=11.96%; N=6.31%

EXAMPLE 18

Following the process described in Example 2, 36 g (100 mmol) of trichlorohexadecylsilane are caused to react with 53 g (310 mmol) of 1,2,2,6,6-pentamethyl-4-piperidinol in 300 ml of dioxane in the presence of 33.3 g (330 ml) of triethylamine.

After cooling to room temperature, the mixture is washed with water and extracted with ethyl ether. After separating off the organic phase and evaporating in vacuo, the compound of the formula

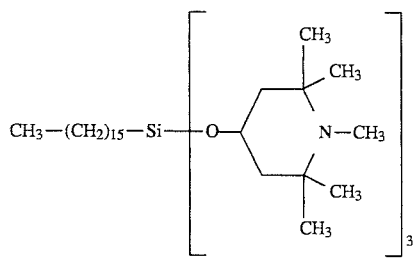

is obtained as a yellowish oil.

Analysis for $C_{46}H_{93}N_3O_3Si$ Calculated: C=72.28%; H=12.26%; N=5.50% Found: C=72.84%; H=12.24%; N=5.36%

EXAMPLE 19

Following the process described in Example 1, 17.9 g (20 mmol) of N,N'-tetrakis[3(diethoxy methyl silyl)propyl]sebacamide are caused to react with 27.6 g (176 mmol) of 2,2,6,6-tetramethyl-4-piperidinol in 100 ml of xylene in the presence of 1.5 ml of Ti(IV) isopropoxide.

After purification by column chromatography the compound of the formula

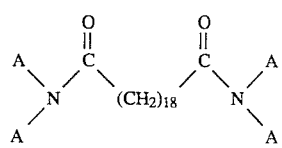

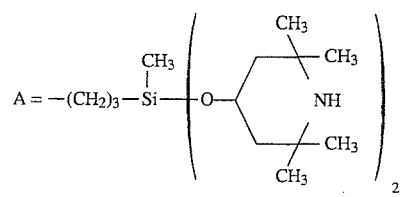

is obtained as a yellowish resin.

Analysis for $C_{98}H_{196}N_{10}O_{10}Si_4$ Calculated: C=65.87%; H=11.05%; N=7.83% Found: C=65.81%; H=11.03%; N=7.79%

EXAMPLE 20

Following the process described in Example 1, 13 g (20 mmol) of 1,3,5-tris[3(diethoxy methyl silyl)propyl]-[1,3,5-triazinane-2,4,6-trione] are caused to react with 20.8 g (132 mmol) of 2,2,6,6-tetramethyl-4-piperidinol in 100 ml of xylene in the presence of 1.5 ml of Ti(IV) isopropoxide.

After purification by washing with water and drying, the compound of the formula

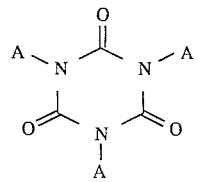

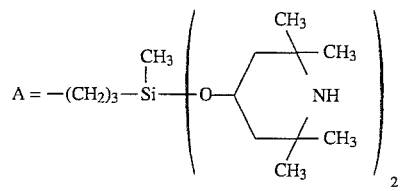

is obtained as a yellowish resin.

Analysis for $C_{69}H_{135}N_9O_9Si_3$ Calculated: C=62.83%; H=10.32%; N=9.56% Found: C=62.29%; H=10.20%; N=9.41%

EXAMPLE 21

(light stabilising action in polypropylene plaques) 1 g of each of the compounds indicated in Table 1, 1 g of tris(2, 4-di-t-butylphenyl) phosphite, 0.5 g of pentaerythritol tetrakis[3-(3,5-di-t-butyl-4-hydroxyphenyl)propionate], 1 g of calcium stearate and 1 g of Filofin Blue G are mixed in a slow mixer with 1000 g of polypropylene powder having a melt index=4 g/10 min (measured at 230° C. and 2.16 kg).

The mixtures obtained are extruded at a temperature of 200°–230° C. to give polymer granules which are subsequently converted to plaques of 2 mm thickness by means of injection moulding at 200°–220° C.

The plaques obtained are exposed in a Weather-O-Meter model 65 WR (ASTM D2565-85) with a black panel temperature of 63° C., until surface crazing (chalking) starts.

By way of comparison, a polypropylene plaque prepared under the same conditions as indicated above, but without the addition of the compounds of the invention, is exposed.

Table 1 shows the exposure time in hours required to bring about this start of chalking.

TABLE 1

| Stabiliser | T chalking (hours) |
|---|---|
| Without stabiliser | 750 |
| Compound of Example 1 | 4260 |
| Compound of Example 3 | 4900 |
| Compound of Example 4 | 3930 |
| Compound of Example 5 | 3310 |
| Compound of Example 7 | 4050 |
| Compound of Example 10 | 3820 |
| Compound of Example 11 | 4260 |
| Compound of Example 12 | 3400 |
| Compound of Example 13 | 3200 |
| Compound of Example 16 | >3900 |
| Compound of Example 17 | >3900 |

EXAMPLE 22

(light stabilising action in polypropylene tapes)

1 g of each of the compounds indicated in Table 2, 1.0 g of tris(2,4-di-t-butylphenyl)phosphite, 0.5 g of pentaerythritol tetrakis[3-(3,5-di-t-butyl-4-hydroxyphenyl)propionate] and 1 g of calcium stearate are mixed in a slow mixer with 1000 g of polypropylene powder having a melt index =2 g/10 min (measured at 230° C. and 2.16 kg).

The mixtures are extruded at 200°–220° C. to give polymer granules which are subsequently converted to stretched tapes of 50 gm thickness and 2.5 mm width, using a semi-industrial type of apparatus (Leonard-Sumirago (VA) Italy), and working under the following conditions:

| Extruder temperature: | 210–230° C. |
|---|---|
| Head temperature: | 240–260° C. |
| Stretch ratio: | 1:6 |

The tapes thus prepared are mounted on white card and exposed in a Weather-O-Meter 65 WR (ASTM D2565-85) with a black panel temperature of 63° C.

The residual tenacity is measured, by means of a constant velocity tensometer, on samples taken after various light exposure times; from this, the exposure time (in hours) required to halve the initial tenacity ($T_{50}$) is measured. By way of comparison, tapes prepared under the same conditions as indicated above, but without the addition of the stabilisers of the present invention, are exposed.

The results obtained are shown in Table 2.

TABLE 2

| Stabiliser | $T_{50}$ (hours) |
|---|---|
| Without stabiliser | 530 |
| Compound of Example 3 | 4810 |
| Compound of Exwnple 7 | 4950 |
| Compound of Example 10 | 3680 |
| Compound of Example 12 | 4210 |
| Compound of Example 13 | >3700 |
| Compound of Example 16 | >3700 |
| Compound of Example 17 | >4070 |

What is claimed is:

1. A compound of formula (I)

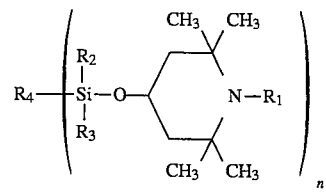

in which $R_1$ is hydrogen, $C_1$–$C_8$alkyl, OH, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or substituted on the phenyl with 1,2 or 3 $C_1$–$C_4$alkyl, or aliphatic $C_1$–$C_8$acyl;

$R_2$ and $R_3$, which may be identical or different, are $C_1$–$C_8$alkyl, phenyl, $C_1$–$C_8$alkoxy or a group of formula (II)

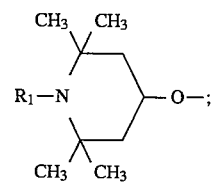

n is 1, 2, 3 or 4; if n is 1, $R_4$ is $C_{12}$–$C_{18}$alkyl, $C_5$–$C_{12}$ cycloalkyl which is unsubstituted or substituted with 1, 2 or 3 $C_1$–$C_4$alkyl or one of the groups of formulae (IIIa)–(IIId)

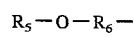

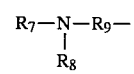

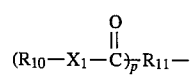

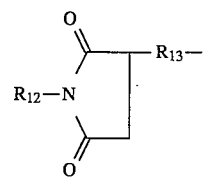

in which $R_5$ is $C_1$–$C_{18}$alkyl, $C_3$–$C_{30}$alkyl interrupted by one or more oxygen atoms, $C_5$–$C_{12}$cycloalkyl which is unsubstituted or substituted with 1,2 or 3 $C_1$–$C_4$alkyl, phenyl which is unsubstituted or substituted with 1, 2 or 3 $C_1$–$C_4$alkyl or with $C_1$–$C_4$alkoxy, $C_7$–$C_9$phenylalkyl which is unsubstituted or substituted on the phenyl with 1, 2 or 3 $C_1$–$C_4$alkyl, a group of formula (IV)

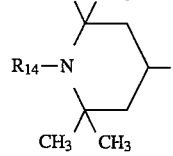

where $R_{14}$ has any one of the meanings given for $R_1$, or $R_5$ is aliphatic, cycloaliphatic or aromatic acyl containing not more than 22 carbon atoms or a group

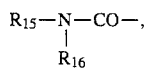

where $R_{15}$ and $R_{16}$, which may be identical or different, are hydrogen, $C_1$–$C_{18}$alkyl, $C_5$–$C_{12}$cycloalkyl which is unsubstituted or substituted with 1, 2 or 3 $C_1$–$C_4$alkyl, $C_7$–$C_9$phenylalkyl which is unsubstituted or substituted on the phenyl with 1, 2 or 3 $C_1$–$C_4$alkyl or a group of formula (IV), or

is a heterocyclic group with 5–7 members, or one of the groups of formulae (Va)–(Vc)

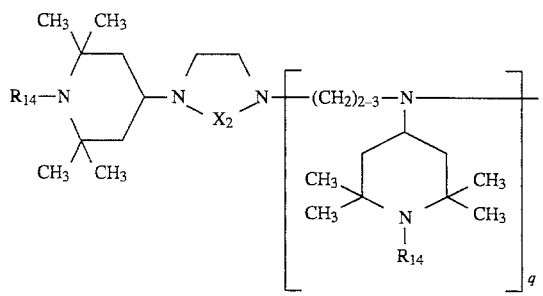

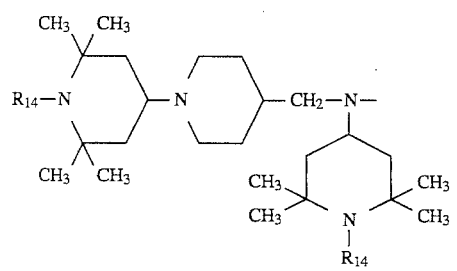

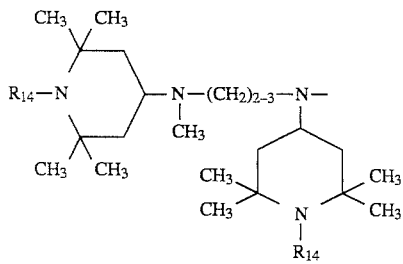

in which $R_{14}$ is as defined above, $X_2$ is —$CH_2CH_2$—, —CO—, —COCO— or —COCH$_2$CO— and q is zero or 1; $R_6$ is $C_2$–$C_{18}$alkylene; $R_7$ and $R_8$, which may be identical or different, are as defined above for $R_{15}$ and $R_{16}$, or $R_7$ is also ($C_1$–$C_{18}$alkoxy)carbonyl or aliphatic, cycloaliphatic or aromatic acyl containing not more than 22 carbon atoms, or

is a heterocyclic group having 5–7 members or one of the groups of formulae (Va)–(Vc) or one of the groups of formulae (VIa)–(VIc)

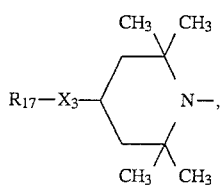

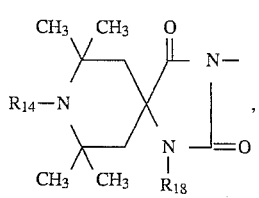

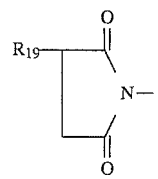

in which $X_3$ is —O— or

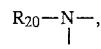

where $R_{20}$ is as defined above for $R_{15}$ and $R_{16}$; $R_{17}$ is as defined above for $R_7$ or $R_{17}$—$X_3$— is hydrogen or a nitrogen-containing heterocyclic group having 5–7 members, with the free valency on the nitrogen atom, or the group

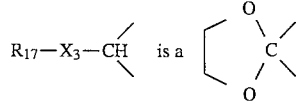

group, $R_{14}$ is as defined above, $R_{18}$ is hydrogen, methyl, acetyl or benzyl and $R_{19}$ is hydrogen or $C_1$–$C_{30}$alkyl; $R_9$ is $C_3$–$C_{18}$alkylene; $R_{10}$ is $C_1$–$C_{18}$alkyl, $C_5$–$C_{12}$cycloalkyl which is unsubstituted or substituted with 1, 2 or 3 $C_1$–$C_4$alkyl, $C_7$–$C_9$phenylalkyl which is unsubstituted or substituted on the phenyl with 1, 2 or 3 $C_1$–$C_4$alkyl or a group of formula (IV), or $R_{10}$ is a group of formula (VII)

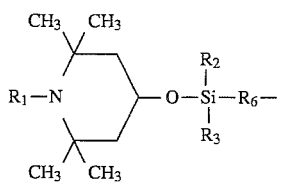

with $R_1$, $R_2$, $R_3$ and $R_6$ as defined above; $X_1$ is as defined above for $X_3$ or $R_{10}X_1$— is a nitrogen-containing heterocyclic group having 5–7 members, with the free valency on the nitrogen atom, or one of the groups of formulae (Va)–(Vc) or (VIa)–(VIc); p is 1, 2 or 3 and, if p is 1, $R_{11}$ is $C_2$–$C_{18}$alkylene, if p is 2, $R_{11}$ is $C_2$–$C_{20}$alkanetriyl, $C_5$–$C_7$cycloalkanetriyl or $C_7$–$C_9$bicycloalkanetriyl and, if p is 3, $R_{11}$ is $C_3$–$C_6$alkanetetrayl; $R_{12}$ is as defined above for $R_{15}$ and $R_{16}$ and $R_{13}$ is a direct bond or $C_1$–$C_{30}$alkylene; if n is 2, $R_4$ is $C_2$–$C_{12}$alkylene, $C_4$–$C_{22}$alkylene interrupted by an oxygen atom or by an

group, where $R_{21}$ is as defined above for $R_7$, or $R_4$ is one of the groups of formulae (VIIIa)–(VIIIc)

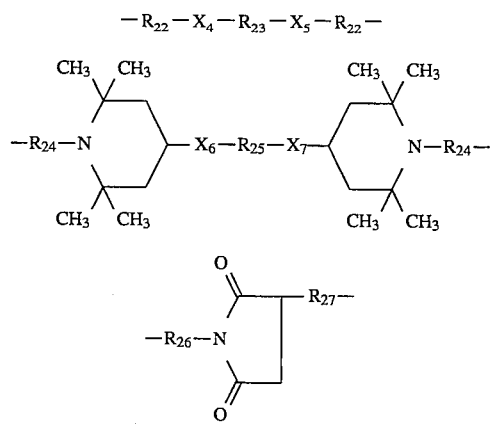

in which $X_4$ and $X_5$, which may be identical or different, are —O— or

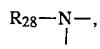

where $R_{28}$ is as defined above for $R_7$; $R_{22}$ is $C_2$–$C_{18}$alkylene or a —$C_rH_{2r}CO$— group, where r is an integer from 2 to 18 and the carbonyl group is bonded to $X_4$ or $X_5$; $R_{23}$ is $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), isopropylidenedicyclohexylene, phenylene which is unsubstituted or substituted by 1 or 2 $C_1$–$C_4$alkyl, phenylenedi($C_1$–$C_4$alkylene), $C_2$–$C_4$alkylidenediphenylene or a group of formula (IXa) or (IXb)

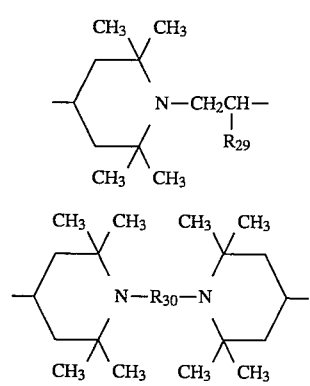

in which $R_{29}$ is hydrogen or $C_1$–$C_4$alkyl and $R_{30}$ is $C_2$–$C_{12}$alkylene, $C_4$–$C_{12}$alkylene interrupted by one or more oxygen atoms or phenylenedi($C_1$–$C_4$alkylene) or, if $R_{22}$ is $C_2$–$C_{18}$alkylene, $R_{23}$ is also carbonyl, a

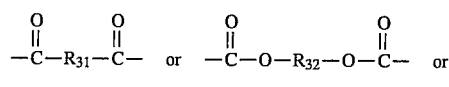

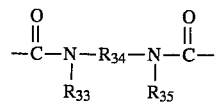

group, where $R_{31}$ is a direct bond, $C_1$–$C_{12}$alkylene, $C_2$–$C_{20}$alkylidene, $C_5$–$C_7$cycloalkylene or phenylene which is unsubstituted or substituted with 1 or 2 $C_1$–$C_4$alkyl, $R_{32}$ and $R_{34}$ are $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), $C_2$–$C_4$alkylenedi($C_5$–$C_7$cycloalkylene ) or a group of formula (IXa) or (IXb), and $R_{33}$ and $R_{35}$, which may be identical or different, are as defined above for $R_{15}$ and $R_{16}$, or the —$R_{23}$—$X_5$— group is a

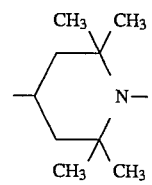

group or the —$X_4$—$R_{23}$—$X_5$— group is a

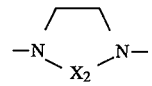

group with $X_2$ as defined above or a

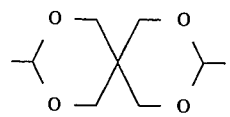

group; $R_{24}$ is $C_3$–$C_{18}$alkylene; $X_6$ and $X_7$, which may be identical or different, are as defined above for $X_4$ and $X_5$; $R_{25}$ is $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene ), carbonyl, or a

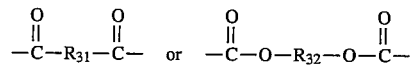

group, with $R_{31}$ and $R_{32}$ as defined above, or the —$X_6$—$R_{25}$—$X_7$— group is an

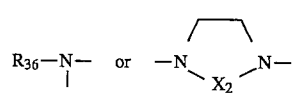

group, where $R_{36}$ is as defined above for $R_7$ and $X_2$ is as defined above, or the

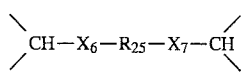

group is a

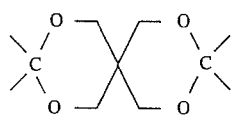

group; $R_{26}$ is $C_3$–$C_{18}$alkylene or a group of formula (X)

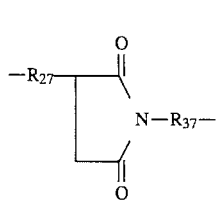
(X)

where $R_{37}$ is $C_2$–$C_{12}$alkylene, $C_4$–$C_{12}$alkylene interrupted by one or more oxygen atoms, $C_5$–$C_7$cycloalkylene, $C_5$–$C_7$cycloalkylenedi($C_1$–$C_4$alkylene) or $C_1$–$C_4$alkylenedi($C_5$–$C_7$cycloalkylene) and $R_{27}$ is a direct bond or $C_1$–$C_{30}$alkylene; if n is 3, $R_4$ is one of the groups of formulae (XIa)–(XIe)

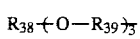
(XIa)

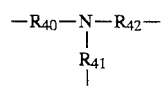
(XIb)

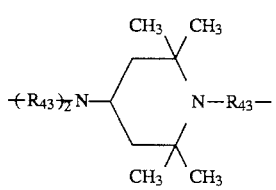
(XIc)

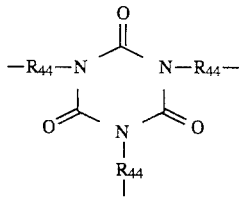
(XId)

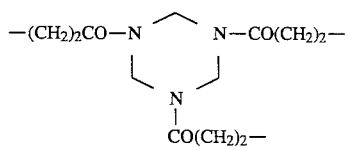
(XIe)

which $R_{38}$ is $C_3$–$C_{12}$alkanetriyl or aliphatic or aromatic triacyl containing not more than 12 carbon atoms; $R_{39}$ is $C_2$–$C_{18}$alkylene or, if $R_{38}$ is $C_3$–$C_{12}$alkanetriyl, $R_{39}$ is also a —$C_sH_{2s}CO$— group where s is an integer from 2 to 18 and the carbonyl group is bonded to the oxygen atom; $R_{40}$, $R_{41}$ and $R_{42}$, which may be identical or different, are $C_3$–$C_{18}$alkylene or $R_{40}$ is also a

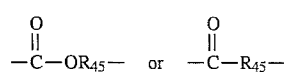

group, where the carbonyl group is bonded to the nitrogen atom and $R_{45}$ is $C_2$–$C_{18}$alkylene; $R_{43}$ is $C_3$–$C_{18}$alkylene and $R_{44}$ is $C_2$–$C_6$alkylene; if n is 4, $R_4$ is one of the groups of formulae (XIIa)–(XIIc)

$$R_{46}\text{+}OR_{47}\text{)}_{\overline{4}} \quad \text{(XIIa)}$$

$$\text{+}R_{48}\text{)}_2\text{—N—}R_{49}\text{—N—}(R_{48}\text{)}_{\overline{2}} \quad \text{(XIIb)}$$

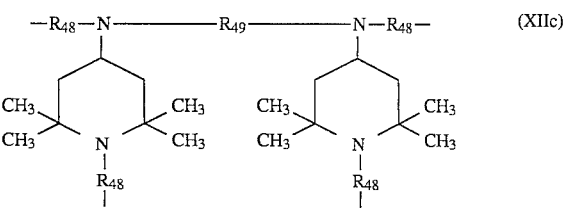
(XIIc)

in which $R_{46}$ is $C_4$–$C_6$alkanetetrayl or aliphatic or aromatic tetraacyl containing not more than 12 carbon atoms; $R_{47}$ is $C_2$–$C_{18}$alkylene or, if $R_{46}$ is $C_4$–$C_1$–$C_{12}$alkanetetrayl, $R_{47}$ is also a —$C_sH_{2s}CO$— group as defined above; $R_{48}$ is $C_3$–$C_{18}$alkylene and $R_{49}$ is as defined above for $R_{25}$.

2. A compound of formula (I) according to claim 1, in which $R_1$ and $R_{14}$ are hydrogen, $C_1$–$C_4$alkyl, OH, $C_6$–$C_{12}$alkoxy, $C_5$–$C_8$cycloalkoxy, allyl, benzyl or acetyl.

3. A compound of formula (I) according to claim 1, in which $R_2$ and $R_3$, which may be identical or different, are $C_1$–$C_4$alkyl, $C_1$–$C_4$alkoxy or a group of formula (II), n is 1,2,3 or 4 and, if n is 1, $R_4$ is $C_{12}$–$C_{18}$alkyl, $C_5$–$C_8$cycloalkyl which is unsubstituted or substituted with 1,2 or 3 $C_1$–$C_4$alkyl, or one of the groups of the formulae (IIIa)–(IIId) in which $R_5$ is $C_4$–$C_{18}$alkyl, $C_4$–$C_{28}$alkyl interrupted by one or more oxygen atoms, $C_5$–$C_8$cycloalkyl which is unsubstituted or substituted with 1,2 or 3 $C_1$–$C_4$alkyl, phenyl which is unsubstituted or substituted with 1,2 or 3 $C_1$–$C_4$alkyl or with $C_1$–$C_4$alkoxy, benzyl which is unsubstituted or substituted on the phenyl with 1,2 or 3 $C_1$–$C_4$alkyl, a group of formula (IV),aliphatic, cycloaliphatic or aromatic acyl containing not more than 20 carbon atoms or an

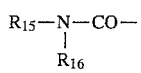

group, where $R_{15}$ and $R_{16}$, which may be identical or different, are hydrogen, $C_1$–$C_{18}$alkyl, $C_5$–$C_8$cycloalkyl which is unsubstituted or substituted with 1,2 or 3 $C_1$–$C_4$alkyl, benzyl which is unsubstituted or substituted on the phenyl with 1,2 or 3 $C_1$–$C_4$alkyl or a group of formula (IV), or

is 4-morpholinyl or one of the groups of formulae (Va)–(Vc), in which $X_2$ is —$CH_2CH_2$— or —CO— or —COCO— and q is zero or 1; $R_6$ is $C_2$–$C_{18}$alkylene; $R_7$ and $R_8$, which may be identical or different, are as defined above for $R_{15}$ and $R_{16}$, or $R_7$ is also ($C_2$–$C_{18}$alkoxy)carbonyl or aliphatic, cycloaliphatic or aromatic acyl containing not more than 20 carbon atoms, or

is 4-morpholinyl or one of the groups of formulae (Va)–(Vc) or one of the groups of formulae (VIa)–(VIc) in which $X_3$ is —O— or

where $R_{20}$ is as defined above for $R_{15}$ and $R_{16}$; $R_{17}$ is as defined above for $R_7$ or $R_{17}X_3$— is hydrogen or 4-morpholinyl, $R_{18}$ is hydrogen or methyl and $R_{19}$ is hydrogen or $C_3$–$C_{28}$alkyl; $R_9$ is $C_3$–$C_{18}$alkylene; $R_{10}$ is $C_2$–$C_{18}$alkyl, $C_5$–$C_8$cycloalkyl which is unsubstituted or substituted with 1,2 or 3 $C_1$–$C_4$alkyl, benzyl which is unsubstituted or substituted on the phenyl with 1,2 or 3 $C_1$–$C_4$alkyl, a group of formula (IV) or a group of formula (VII), $X_1$ is as defined above for $X_3$ or $R_{10}X_1$— is 4-morpholinyl or one of the groups of formulae (Va)–(Vc) or (VIa)–(VIc); p is 1,2 or 3 and, if p is 1, $R_{11}$ is $C_2$–$C_{17}$alkylene and, if p is 2, $R_{11}$ is $C_2$–$C_{20}$alkanetriyl or $C_6$–$C_7$cycloalkanetriyl and, if p is 3, $R_{11}$ is propanetetrayl; $R_{12}$ is as defined above for $R_{15}$ and $R_{16}$ and $R_{13}$ is a direct bond or $C_3$–$C_{28}$alkylene; if n is 2, $R_4$ is $C_2$–$C_8$alkylene or $C_4$–$C_{21}$alkylene interrupted by an oxygen atom or by an

group, where $R_{21}$ is as defined above for $R_7$, or $R_4$ is one of the groups of formulae (VIIIa)–(VIIIc), in which $X_4$ and $X_5$, which may be identical or different, are —O—

where $R_{28}$ is as defined above for $R_7$; $R_{22}$ is $C_2$–$C_{18}$alkylene or a $C_rH_{2r}CO$— group, where r is an integer from 2 to 17 and the carbonyl group is bonded to $X_4$ or $X_5$; $R_{23}$ is $C_2$–$C_{10}$alkylene or $C_4$–$C_{10}$alkylene interrupted by 1,2 or 3 oxygen atoms, cyclohexylene, cyclohexylenedimethylene, methylenedicyclohexylene, isopropylidenedicyclohexylene, phenylene, phenylenedimethylene, isopropylidenediphenylene or a group of formula (IXa) or (IXb) in which $R_{29}$ is hydrogen or methyl and $R_{30}$ is $C_2$–$C_{10}$alkylene, $C_4$–$C_{10}$alkylene interrupted by 1,2 or 3 oxygen atoms or phenylenedimethylene or, if $R_{22}$ is $C_2$–$C_{18}$alkylene, $R_{23}$ is also carbonyl or a

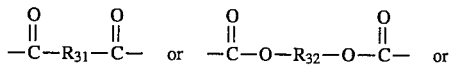

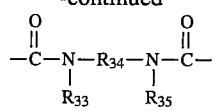

group, where $R_{31}$ is $C_1$–$C_{10}$alkylene, $C_3$–$C_{19}$alkylidene, cyclohexylene or phenylene, $R_{32}$ and $R_{34}$ are $C_2$–$C_{10}$alkylene, $C_4$–$C_{10}$alkylene interrupted by 1,2 or 3 oxygen atoms, cyclohexylene, cyclohexylenedimethylene, methylenedicyclohexylene, isopropylidenedicyclohexylene or a group of formula (IXa) or (IXb) and $R_{33}$ and $R_{35}$, which may be identical or different, are as defined above for $R_{15}$ and $R_{16}$ or the —$R_{23}$—$X_5$— group is a

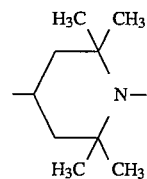

group or the —$X_4$—$R_{23}$—$X_5$— group is a 1,4-piperazinediyl group or a

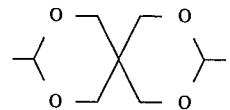

group; $R_{24}$ is $C_3$–$C_{18}$alkylene; $X_6$ and $X_7$, which may be identical or different, are as defined above for $X_4$ and $X_5$, $R_{25}$ is $C_2$–$C_{10}$alkylene, $C_4$–$C_{10}$alkylene interrupted by 1,2 or 3 oxygen atoms, cyclohexylene, cyclohexylenedimethylene, methylenedicyclohexylene, carbonyl or a

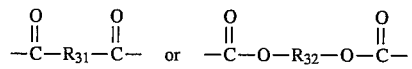

group, with $R_{31}$ and $R_{32}$ as defined above, or the —$X_6$—$R_{25}$—$X_7$— group is an

group, where $R_{36}$ is as defined above for $R_7$; $R_{26}$ is $C_3$–$C_{18}$alkylene or a group of formula (X), where $R_{37}$ is $C_2$–$C_{10}$alkylene, $C_4$–$C_{10}$alkylene interrupted by 1,2 or 3 oxygen atoms, cyclohexylene, cyclohexylenedimethylene or methylenedicyclohexylene and $R_{27}$ is a direct bond or $C_3$–$C_{28}$alkylene; if n is 3, $R_4$ is one of the groups of formulae (XIa)–(XIe), in which $R_{38}$ is $C_3$–$C_{10}$alkanetriyl or aliphatic or aromatic triacyl containing not more than 10 carbon atoms; $R_{39}$ is $C_2$–$C_{18}$alkylene or, if $R_{38}$ is $C_3$–$C_{10}$alkanetriyl, $R_{39}$ is also a —$C_sH_{2s}CO$— group, where s is an integer from 2 to 17 and the carbonyl group is bonded to the oxygen atom; $R_{40}$, $R_{41}$ and $R_{42}$, which may be identical or different, are $C_3$–$C_{18}$alkylene or $R_{40}$ is also a

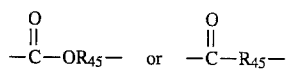

group, where the carbonyl group is bonded to the nitrogen atom and $R_{45}$ is $C_2$–$C_{18}$alkylene; $R_{43}$ is $C_3$–$C_{11}$alkylene and $R_{44}$ is $C_2$–$C_5$alkylene; if n is 4, $R_4$ is one of the groups of formulae (XIIa)–(XIIc) in which $R_{46}$ is $C_4$–$C_6$alkanetetrayl or aliphatic or aromatic tetraacyl containing not more than 10 carbon atoms, $R_{47}$ is $C_2$–$C_{18}$alkylene or, if $R_{46}$ is $C_4$–$C_6$alkanetetrayl, $R_{47}$ is also a —$C_sH_{2s}CO$— group as defined above; $R_{48}$ is $C_3$–$C_{11}$alkylene and $R_{49}$ is as defined above for $R_{25}$.

4. A compound of formula (I) according to claim 1, in which $R_2$ and $R_3$, which may be identical or different, are methyl, ethyl, methoxy, ethoxy or a group of formula (II), n is 1, 2, 3 or 4 and, if n is 1, $R_4$ is $C_{12}$–$C_{18}$alkyl, cyclohexyl which is unsubstituted or substituted with 1, 2 or 3 $C_1$–$C_4$alkyl or one of the groups of formulae (IIIa)–(IIId), in which $R_5$ is $C_6$–$C_{18}$alkyl, $C_6$–$C_{24}$alkyl interrupted by one or more oxygen atoms, cyclohexyl which is unsubstituted or substituted with 1, 2 or 3 $C_1$–$C_4$alkyl, benzyl, a group of formula (IV), aliphatic, cycloaliphatic or aromatic acyl containing not more than to 18 carbon atoms or an

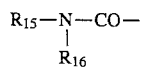

group where $R_{15}$ and $R_{16}$, which may be identical or different, are $C_1$–$C_{18}$alkyl, cyclohexyl which is unsubstituted or substituted with 1, 2 or 3 $C_1$–$C_4$alkyl, benzyl or a group of formula (IV) or

is one of the groups of formulae (Va)–(Vc), in which $X_2$ is —$CH_2CH_2$— or —CO— or —COCO— and q is zero or 1; $R_6$ is $C_2$–$C_{11}$alkylene; $R_7$ and $R_8$, which may be identical or different, are as defined above for $R_{15}$ and $R_{16}$ or hydrogen or $R_7$ is also ($C_4$–$C_{18}$alkoxy)carbonyl or aliphatic, cycloaliphatic or aromatic acyl containing not more than 18 carbon atoms, or

is one of the groups of formulae (Va)–(Vc) or one of the groups of formulae (VIa)–(VIc), in which $X_3$ is —O— or

where $R_{20}$ is as defined above for $R_{15}$ and $R_{16}$; $R_{17}$ is as defined above for $R_7$ or $R_{17}X_3$— is hydrogen, $R_{18}$ is hydrogen or methyl and $R_{19}$ is hydrogen or $C_3$–$C_{24}$alkyl; $R_9$ is $C_3$–$C_{11}$alkylene; $R_{10}$ is $C_4$–$C_{18}$alkyl, cyclohexyl which is unsubstituted or substituted with 1, 2 or 3 $C_1$–$C_4$alkyl, benzyl, a group of formula (IV) or a group of formula (VII), $X_1$ is as defined above for $X_3$ or $R_{10}X_1$— is one of the groups of formulae (Va)–(Vc) or (VIa)–(VIc); p is 1 or 2 and, if p is 1, $R_{11}$ is $C_2$–$C_{17}$alkylene and, if p is 2, $R_{11}$ is $C_2$–$C_{16}$alkanetriyl; $R_{12}$ is as defined above for $R_{15}$ and $R_{16}$ and $R_{13}$ is a direct bond or $C_3$–$C_{24}$alkylene; if n is 2, $R_4$ is $C_2$–$C_6$alkylene or $C_4$–$C_{14}$alkylene interrupted by an oxygen atom or by an

group, where $R_{21}$ is as defined above for $R_7$ or $R_4$ is one of the groups of formulae (VIIIa)–(VIIIc) in which $X_4$ and $X_5$, which may be identical or different, are —O— or

where $R_{28}$ is as defined above for $R_7$; $R_{22}$ is $C_2$–$C_{11}$alkylene or a —$C_rH_{2r}CO$— group, where r is an integer from 2 to 10 and the carbonyl group is bonded to $X_4$ or $X_5$, $R_{23}$ is $C_2$–$C_8$alkylene, $C_4$–$C_{10}$alkylene interrupted by 1, 2 or 3 oxygen atoms, cyclohexylene, cyclohexylenedimethylene, methylenedicyclohexylene, phenylene, phenylenedimethylene or a group of formula (IXa), in which $R_{29}$ is hydrogen or methyl or, if $R_{22}$ is $C_2$–$C_{11}$alkylene, $R_{23}$ is also carbonyl, or a

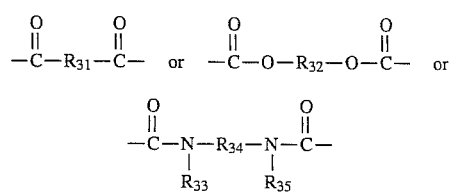

group, where $R_{31}$ is $C_2$–$C_8$alkylene, $C_5$–$C_{13}$alkylidene, cyclohexylene or phenylene, $R_{32}$ and $R_{34}$ are $C_2$–$C_8$alkylene, $C_4$–$C_{10}$alkylene interrupted by 1, 2 or 3 oxygen atoms, cyclohexylene, cyclohexylenedimethylene, methylenedicyclohexylene or a group of formula (IXa) and $R_{33}$ and $R_{35}$, which may be identical or different, are as defined above for $R_{15}$ and $R_{16}$ or the —$R_{23}$—$X_5$— group is a

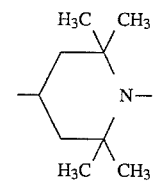

group; $R_{24}$ is $C_3$–$C_{11}$alkylene; $X_6$ and $X_7$, which may be identical or different, are as defined above for $X_4$ and $X_5$, $R_{25}$ is $C_2$–$C_8$alkylene, $C_4$–$C_{10}$alkylene interrupted by 1, 2 or 3 oxygen atoms, cyclohexylene, cyclohexylenedimethylene, methylenedicyclohexylene, carbonyl or a

group, with $R_{31}$ and $R_{32}$ as defined above, or the group —$X_6$—$R_{25}$—$X_7$— is an

group, where $R_{36}$ is as defined above for $R_7$, $R_{26}$ is $C_3$–$C_{11}$alkylene or a group of formula (X), where $R_{37}$ is $C_2$–$C_8$alkylene, $C_4$–$C_{10}$alkylene interrupted by 1,2 or 3 oxygen atoms, cyclohexylene, cyclohexylenedimethylene or methylenedicyclohexylene and $R_{27}$ is a direct bond or $C_3$–$C_{24}$alkylene; if n is 3, $R_4$ is one of the groups of formulae (XIa)–(XIe), in which $R_{38}$ is $C_3$–$C_8$alkanetriyl or aliphatic $C_4$–$C_7$triacyl; $R_{39}$ is $C_2$–$C_{11}$ alkylene or, if $R_{38}$ is $C_3$–$C_8$alkanetriyl, $R_{39}$ is also a —$C_sH_{2s}CO$— group, where s is an integer from 2 to 10 and the carbonyl group is bonded to the oxygen atom, $R_{40}$, $R_{41}$ and $R_{42}$, which may be identical or different, are $C_3$–$C_{11}$alkylene or $R_{40}$ is also a

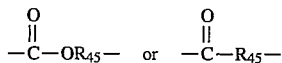

group, where the carbonyl group is bonded to the nitrogen atom and $R_{45}$ is $C_2$–$C_{11}$alkylene, $R_{43}$ is $C_3$–$C_6$alkylene and $R_{44}$ is $C_2$–$C_4$alkylene; if n is 4, $R_4$ is one of the groups of formulae (XIIa)–(XIIc) in which $R_{46}$ is $C_4$–$C_5$alkanetetrayl or aliphatic $C_6$–$C_8$tetraacyl, $R_{47}$ is $C_2$–$C_{11}$alkylene or, if $R_{46}$ is $C_4$–$C_5$alkanetetrayl, $R_{47}$ is also a —$C_sH_{2s}CO$— group as defined above; $R_{48}$ is $C_3$–$C_6$alkylene and $R_{49}$ is as defined above for $R_{25}$.

5. A compound of formula (I) according to claim 1, in which $R_2$ and $R_3$, which may be identical or different, are methyl, methoxy, ethoxy or a group of formula (H), n is 1,2,3 or 4 and, if n is 1, $R_4$ is $C_{12}$–$C_{18}$alkyl, cyclohexyl or one of the groups of formulae (IIIa)–(IIId) in which $R_5$ is $C_8$–$C_{18}$alkyl, $C_{10}$–$C_{22}$alkyl interrupted by 1 or 2 oxygen atoms, cyclohexyl, benzyl, a group of formula (IV), aliphatic $C_8$–$C_{18}$acyl or an

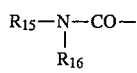

group, where $R_{15}$ and $R_{16}$, which may be identical or different, are $C_4$–$C_{18}$alkyl, cyclohexyl, benzyl or a group of formula (IV), or

is one of the groups of formulae (Va)–(Vc), in which $X_2$ is —$CH_2CH_2$, —CO— or —COCO— and q is zero or 1; $R_6$ is $C_2$–$C_5$alkylene; $R_7$ and $R_8$, which may be identical or different, are as defined above for $R_{15}$ and $R_{16}$ or are hydrogen, or $R_7$ is also ($C_8$–$C_{18}$alkoxy)carbonyl or aliphatic $C_8$–$C_{18}$acyl or

is one of the groups of formulae (Va)–(Vc) or one of the groups of formulae (VIa)–(VIc), in which $X_3$ is —O— or

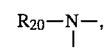

where $R_{20}$ is as defined above for $R_{15}$ and $R_{16}$; $R_{17}$ is as defined above for $R_7$, $R_{18}$ is hydrogen and $R_{19}$ is $C_8$–$C_{18}$alkyl; $R_9$ is $C_3$–$C_5$alkylene; $R_{10}$ is $C_8$–$C_{18}$alkyl, cyclohexyl, benzyl, a group of formula (IV) or a group of formula (VII), $X_1$ is as described above for $X_3$ or $R_{10}X_1$— is one of the groups of formulae (Va)–(Vc) or (VIa)–(VIc); p is 1 or 2 and, if p is 1, $R_{11}$ is $C_2$–$C_{10}$alkylene and, if p is 2, $R_{11}$ is $C_2$–$C_{14}$alkanetriyl; $R_{12}$ is as defined above for $R_{15}$ and $R_{16}$ and $R_{13}$ is a direct bond or $C_3$–$C_{18}$alkylene; if n is 2, $R_4$ is $C_2$–$C_4$alkylene, $C_4$–$C_{14}$alkylene interrupted by an oxygen atom or $C_6$–$C_{10}$alkylene interrupted by an

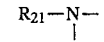

group, where $R_{21}$ is as defined above for $R_7$, or $R_4$ is one of the groups of formulae (VIIIa)–(VIIIc), in which $X_4$ and $X_5$, which may be identical or different, are —O— or

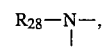

where $R_{28}$ is as defined above for $R_7$; $R_{22}$ is $C_2$–$C_5$alkylene or a —$C_rH_{2r}CO$— group, where r is an integer from 2 to 10 and the carbonyl group is bonded to $X_4$ or $X_5$, $R_{23}$ is $C_2$–$C_6$alkylene, $C_6$–$C_{10}$alkylene interrupted by 2 or 3 oxygen atoms, cyclohexylenedimethylene, methylenedicyclohexylene or a group of formula (IXa), in which $R_{29}$ is hydrogen or, if $R_{22}$ is $C_2$–$C_5$alkylene, $R_{23}$ is also carbonyl

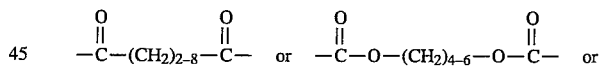

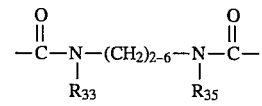

group where $R_{33}$ and $R_{35}$ are a group of formula (IV), or the —$R_{23}$—$X_5$ group is a

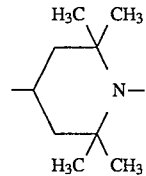

group; $R_{24}$ is $C_3$–$C_5$alkylene; $X_6$ and $X_7$ are as defined above for $X_4$ and $X_5$; $R_{25}$ is $C_2$–$C_6$alkylene, $C_6$–$C_{10}$alkylene interrupted by 2 or 3 oxygen atoms, cyclohexylenedimethylene, methylenedicyclohexylene or a

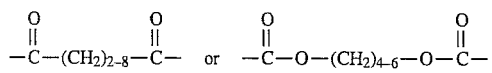

group; $R_{26}$ is $C_3$–$C_5$ alkylene or a group of formula (X), where $R_{37}$ is $C_2$–$C_{10}$alkylene, $C_6$–$C_{10}$alkylene interrupted by 2 or 3 oxygen atoms, cyclohexylenedimethylene or methylenedicyclohexylene and $R_{27}$ is a direct bond or $C_3$–$C_{18}$alkylene; if n is 3, $R_4$ is one of the groups of formulae (XIa)–(XIe), in which $R_{38}$ is $C_3$–$C_6$alkanetriyl or aliphatic $C_5$–$C_7$triacyl; $R_{39}$ is $C_2$–$C_5$alkylene or, if $R_{38}$ is $C_3$–$C_6$alkanetriyl, $R_{39}$ is also a —$C_sH_{2s}CO$— group, where s is an integer from 2 to 10 and the carbonyl group is bonded to the oxygen atom; $R_{40}$, $R_{41}$ and $R_{42}$, which may be identical or different, are $C_3$–$C_5$alkylene, or $R_{40}$ is also a

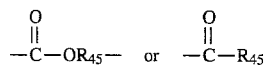

group, where the carbonyl group is bonded to the nitrogen atom and $R_{45}$ is $C_2$–$C_{11}$alkylene; $R_{43}$ is $C_3$–$C_5$alkylene and $R_{44}$ is $C_2$–$C_4$alkylene; if n is 4, $R_4$ is one of the groups of formulae (XIIa)–(XIIc), in which $R_{46}$ is a

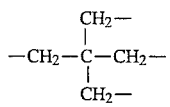

group, $R_{47}$ is $C_2$–$C_5$alkylene; $R_{48}$ is $C_3$–$C_5$alkylene and $R_{49}$ is as defined above for $R_{25}$.

6. A compound of formula (I) according to claim 1, in which $R_1$ and $R_{14}$ are hydrogen or methyl, $R_2$ and $R_3$, which may be identical or different, are methyl or a group of formula (II), n is 1,2,3, or 4 and, if n is 1, $R_4$ is $C_{12}$–$C_{18}$alkyl or one of the groups of formulae (IIIa)–(IIId) in which $R_5$ is $C_{12}$–$C_{18}$alkyl, a group of formula (IV), aliphatic $C_{12}$–$C_{18}$acyl or an

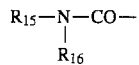

group, where $R_{15}$ and $R_{16}$, which may be identical or different, are $C_4$–$C_{12}$alkyl or a group of formula (IV), $R_6$ is ethylene or trimethylene, $R_7$ and $R_8$, which may be identical or different, are as defined above for $R_{15}$ or $R_{16}$ or hydrogen, or

is a group of formula (Va), in which $X_2$ is —$CH_2CH_2$— or —CO— and q is zero or 1, or a group of formula (VIb) in which $R_{18}$ is hydrogen, $R_9$ is trimethylene, $R_{10}$ is a group of formula (IV), $X_1$ is —O— or —NH—, p is 1 or 2 and, if p is 1, $R_{11}$ is $C_2$–$C_{10}$alkylene and, if p is 2, $R_{11}$ is $C_2$–$C_4$alkanetriyl, $R_{12}$ is $C_{12}$–$C_{18}$ alkyl and $R_{13}$ is a direct bond; if n is 2, $R_4$ is a

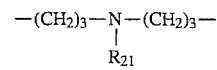

group; where $R_{21}$ is $C_{12}$–$C_{18}$alkyl, ($C_{12}$–$C_{18}$alkoxy)carbonyl or aliphatic $C_{12}$–$C_{18}$acyl, or $R_4$ is one of the groups of formulae (VIIIa)–(VIIIc), in which $X_4$ and $X_5$ are

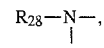

where $R_{28}$s is a group of formula (IV), $R_{22}$ is trimethylene or a —$CH_2CH_2CO$— group, with the carbonyl group bonded to $X_4$ or $X_5$, $R_{23}$ is —$(CH_2)_{2-6}$—, $R_{24}$ is trimethylene, $X_6$ and $X_7$ are —O—, $R_{25}$ is

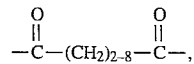

$R_{26}$ is a group of formula (X), in which $R_{37}$ is —$(CH_2)_{2-6}$— and $R_{27}$ is a direct bond; if n is 3, $R_4$ is one of the groups of formulae (XIa)–(XIe), in which $R_{38}$ is a

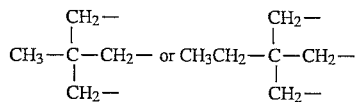

group, $R_{39}$ is trimethylene or a —$CH_2CH_2CO$— group, with the carbonyl group bonded to the oxygen atom and $R_{40}$, $R_{41}$, $R_{42}$, $R_{43}$ and $R_{44}$ are trimethylene; if n is 4, $R_4$ is one of the groups of formulae (XIIa)–(XIIc), in which $R_{46}$ is a

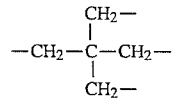

group, $R_{47}$ is $C_2$–$C_5$alkylene; $R_{48}$ is $C_3$–$C_5$alkylene and $R_{49}$ is as defined above for $R_{25}$.

* * * * *